(12) United States Patent
Zhang et al.

(10) Patent No.: US 8,673,890 B2
(45) Date of Patent: Mar. 18, 2014

(54) 2,3-DIHYDRO-1H-ISOINDOL-1-IMINE DERIVATIVES USEFUL AS THROMBIN PAR-1 RECEPTOR ANTAGONIST

(75) Inventors: Han-Cheng Zhang, Lansdale, PA (US); Bruce Maryanoff, Forest Grove, PA (US); Kimberly White, North Wales, PA (US); Stephen C. Yabut, Perkasie, PA (US); Hong Ye, Lansdale, PA (US); Cailin Chen, New Hope, PA (US)

(73) Assignee: Janssen Pharmaceutica NV (BE)

( * ) Notice: Subject to any disclaimer, the term of this patent is extended or adjusted under 35 U.S.C. 154(b) by 477 days.

(21) Appl. No.: 12/913,989

(22) Filed: Oct. 28, 2010

(65) Prior Publication Data

US 2011/0105490 A1    May 5, 2011

Related U.S. Application Data

(60) Provisional application No. 61/256,146, filed on Oct. 29, 2009.

(51) Int. Cl.
*A61K 31/33* (2006.01)
*A61K 31/335* (2006.01)
*C07D 491/02* (2006.01)
*C07D 321/10* (2006.01)

(52) U.S. Cl.
USPC ........... 514/183; 514/450; 540/468; 549/348; 549/349

(58) Field of Classification Search
None
See application file for complete search history.

(56) References Cited

U.S. PATENT DOCUMENTS

| | | |
|---|---|---|
| 2005/0004204 A1 | 1/2005 | Suzuki et al. |
| 2006/0058370 A1 | 3/2006 | Shimomura et al. |
| 2007/0208016 A1 | 9/2007 | Suzuki et al. |
| 2008/0214834 A1 | 9/2008 | Yoshizawa et al. |

FOREIGN PATENT DOCUMENTS

| | | |
|---|---|---|
| JP | 2005249570 A | 9/2005 |
| WO | WO 02/85855 A1 | 4/2002 |
| WO | WO 2004/078721 A1 | 2/2004 |
| WO | WO 2005/084679 A1 | 4/2005 |
| WO | WO 2006/018955 A1 | 7/2006 |
| WO | WO 2009/088063 A1 | 1/2009 |
| WO | WO 2009/097970 A1 | 8/2009 |
| WO | WO 2009/097971 A1 | 8/2009 |
| WO | WO 2009/097972 A1 | 8/2009 |
| WO | WO 2009/097973 A2 | 8/2009 |
| WO | WO 2009/097973 A3 | 8/2009 |

OTHER PUBLICATIONS

"Cancer Prevention Overview", http://www.cancer.gov/cancertopics/pdq/prevention/overview/patient, accessed Apr. 9, 2010.*
Andrade. The Journal of Pharmacology and Experimental Therapeutics, 2001, 298, 34-42.*
Nantermet. Bioorganic and Medicinal Chemistry Letters, 2002, 12, 319-23.*
Vu, T-K. H., et al., "Molecular Cloning of a Functional Thrombin Receptor Reveals a Novel Proteolytic Mechanism of Receptor Activation", *Cell*, 1991, pp. 1057-1068, vol. 64.
Nystedt, S., et al., "Molecular cloning of a potential proteinase activated receptor", *Proc. Natl. Acad. Sci.*, US, 1994, pp. 9208-9212, vol. 91.
Ishihara, H., et al., "Protease-activated receptor 3 is a second thrombin receptor in humans", *Nature*, 1997, pp. 502-506, vol. 386.
Fu, W-F., et al., "Cloning and characterization of human protease-activated receptor 4", *Proc. Natl. Acad. Sci.*, US, 1998, pp. 6642-6646, vol. 95.
Cook, J.J., et al., "Molecular and Cellular Cardiology: An Antivbody Against the Exosite of the Coned Thrombin Receptor Inhibits Experimental Arterial Thrombosis in the African Green Monkey", *Circulation*, 1995, pp. 2961-2971, vol. 91.
Sugama, Y., et al., "Thombin-induced Expression of Endothelial P-Selectin and Intercellular Adhesion Molecule-1: A Mechanism for Stabilizing Neutrophil Adhesion", *J. Cell. Biol.*, 1992, pp. 935-944, vol. 119.
Hung, D.T., "Thrombin-induced Events in Non-Platelet Cells Are Mediated by the Unique Proteolytic Mechanism Established for the Cloned Platelet Thrombin Receptor", *J. Cell Biol.*, 1992, pp. 827-832, vol. 116.
Tatakis, D.N., et al., "Thrombin Effect on Osteoblastic Cells II. Structure-Function Relationships", *Biochem. Biophys. Res. Commun.*, 1991, pp. 181-188, vol. 174.
Jalink, K, et al., "Thrombin Receptor Activation Causes Rapid Neural Cell Rounding and Neurite Retraction Independent of Classic Second Messegners", *J. Cell Biol.*, 1992, pp. 411-419, vol. 118.
Bednar, B., et al., "Platelet Aggregation Monitored ina 96 Well Microplate Reader is Useful for Evaluation of Platelet Agonists and Antagonists", *Thromb. Res.*, 1995, pp. 453-463, vol. 77.

* cited by examiner

*Primary Examiner* — Noble Jarrell
(74) *Attorney, Agent, or Firm* — Yuriy P. Stercho

(57) ABSTRACT

The present invention is directed to novel 2,3-dihydro-1H-isoindol-1-imine derivatives, pharmaceutical compositions containing them and their use in the treatment of disorders and conditions modulated by the thrombin PAR-1 receptor antagonists.

15 Claims, No Drawings

2,3-DIHYDRO-1H-ISOINDOL-1-IMINE DERIVATIVES USEFUL AS THROMBIN PAR-1 RECEPTOR ANTAGONIST

CROSS REFERENCE TO RELATED APPLICATIONS

This application claims the benefit of U.S. Provisional Application 61/256,146, filed on Oct. 29, 2009, which is incorporated by reference herein in its entirety.

FIELD OF THE INVENTION

The present invention is directed to novel 2,3-dihydro-1H-isoindol-1-imine derivatives, pharmaceutical compositions containing them and their use in the treatment of disorders and conditions modulated by the thrombin receptor (PAR-1) antagonists. More particularly, the compounds of the present invention are thrombin receptor (PAR-1) antagonists, useful in the treatment of diseases associated with thrombosis, restenosis, inflammation, stroke, atherosclerosis, ischemic conditions, angiogenesis and related disorders, cancer, and neurodegenerative disorders.

BACKGROUND OF THE INVENTION

Thrombin is an important serine protease that is involved in hemostasis and thrombosis. One of the key actions of thrombin is cellular modulation via receptor activation. A functional human thrombin receptor (PAR-1), cloned by Coughlin in 1991 (T.-K. Vu, *Cell* 1991, 64, 1057), is a member of the G-protein-coupled receptor (GPCR) superfamily. Thrombin receptor activation occurs by N-terminal recognition and proteolytic cleavage to reveal a truncated N-terminus. This new receptor sequence can trigger activation and signal transduction leading to platelet aggregation. Since 1991, three other protease-activated receptors with extensive homology to the thrombin receptor, "PAR-2" (S. Nystedt, *Proc. Natl. Acad. Sci. USA* 1994, 91, 9208), "PAR-3" (H. Ishihara, *Nature* 1997, 386, 502), and "PAR-4" (W.-F. Xu, *Proc. Natl. Acad. Sci. USA* 1998, 95, 6642), have been identified. Thrombin receptor (PAR-1) specific antibody-induced blockade of the platelet thrombin receptor has shown efficacy against arterial thrombosis in vivo (J. J. Cook *Circulation* 1995, 91, 2961). Hence, antagonists of the thrombin receptor (PAR-1) are useful to block these protease-activated receptors and, as such, would be useful for treating platelet-mediated thrombotic disorders, such as myocardial infarction, stroke, restenosis, atherosclerosis, and ischemic conditions.

The thrombin receptor (PAR-1) has also been identified on other cell types, such as endothelial, fibroblast, renal, osteosarcoma, smooth muscle, myocytes, tumor, and neuronal/glial. Thrombin activation of endothelial cells up-regulates P-selectin to induce polymorphonuclear leukocyte adhesion, an inflammatory response of the vessel wall (Y. Sugama, *J. Cell Biol.* 1992, 119, 935). In fibroblasts, thrombin receptor (PAR-1) activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174, 181). Thrombin has been implicated in the regulation and retraction of neurons (K. Jalink, *J. Cell. Biol.* 1992, 118, 411). In this context, the antagonist compounds of this invention may also be useful for treating inflammation, osteoporosis, angiogenesis and related disorders, cancer, neurodegenerative disorders and/or glomerulonephritis.

SUMMARY OF THE INVENTION

The present invention is directed to compounds of formula (I)

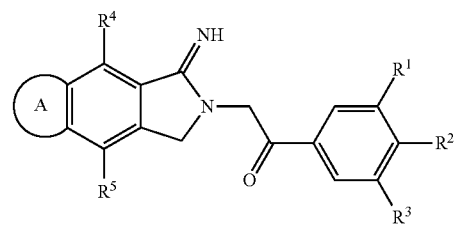

(I)

wherein $R^1$ is $C_{3-6}$alkyl;

$R^2$ is selected from the group consisting of hydroxy and $C_{1-4}$alkoxy;

$R^3$ is selected from the group consisting of hydrogen, halogen, $C_{3-6}$alkyl, 1-pyrrolidinyl, 1-piperidinyl, 1-piperazinyl, 4-morpholinyl and 4-thiomorpholinyl; wherein the 1-pyrrolidinyl, 1-piperidinyl, 1-piperazinyl, 4-morpholinyl or 4-thiomorpholinyl is optionally substituted with $C_{1-4}$alkyl;

alternatively, $R^2$ and $R^3$ are taken together with the carbon atoms to which they are bound to form 2,3-morpholinyl or 2,3-(4-methyl-morpholinyl);

$R^4$ is selected from the group consisting of hydrogen and halogen; and $R^5$ is selected from the group consisting of hydrogen and halogen; provided that $R^4$ and $R^5$ are not each halogen;

is selected from the group consisting of formulas (a) through (e); (wherein the "●" symbols indicate the atoms of attachment to the phenyl portion of the rest of the scaffold);

(a)

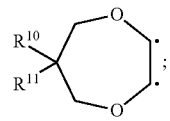

wherein $R^{10}$ is selected from the group consisting of hydrogen, halogen and $C_{1-4}$alkyl; and $R^{11}$ is selected from the group consisting of hydrogen, fluoro, $C_{1-2}$alkyl, —$CH_2$—C(O)H—($C_{1-4}$alkyl)—OH, —$CH_2CH(OC_{1-2}alkyl)_2$ and —($C_{1-4}$alkyl)-$NR^AR^B$;

wherein $R^A$ and $R^B$ are each independently selected from the group consisting of hydrogen and $C_{1-4}$alkyl;

alternatively, $R^A$ and $R^B$ are taken together with the nitrogen atom to which they are bound to form a monocyclic nitrogen-containing heterocyclyl group; and wherein the monocyclic nitrogen-containing heterocyclyl group is optionally substituted with $C_{1-4}$alkyl;

(b)

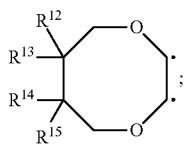

wherein $R^{12}$, $R^{13}$, $R^{14}$ and $R^{15}$ are each hydrogen or are each fluoro;

alternatively, $R^{12}$ and $R^{14}$ are taken together as an electron pair to form a bond between the carbon atoms to which they are bound (to form a double bond between said carbon atoms); and $R^{13}$ and $R^{15}$ are each hydrogen;

alternatively, $R^{12}$ and $R^{14}$ are taken together as an electron pair to form a bond between the carbon atoms to which they are bound (to form a double bond between said carbon atoms); and $R^{13}$ and $R^{15}$ are taken together with the carbon atoms to which they are bound to form a bridging group selected from the group consisting of

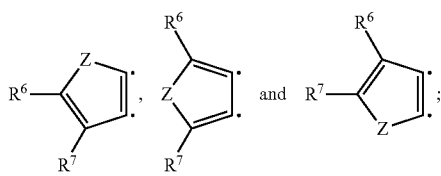

wherein Z is selected from the group consisting of O and S; and wherein $R^6$ and $R^7$ are each independently selected from the group consisting of $C_{1-4}$alkyl and —C(O)O—($C_{1-4}$alkyl);

(c)

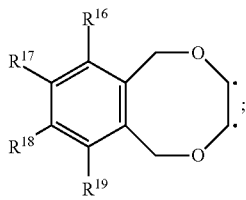

wherein $R^{16}$, $R^{17}$, $R^{18}$ and $R^{19}$ are each independently selected from the group consisting of hydrogen, halogen, nitro, $C_{1-4}$alkyl, —C(O)OH and —C(O)O—($C_{1-4}$alkyl); provided that at least two of $R^{16}$, $R^{17}$, $R^{18}$ and $R^{19}$ are hydrogen;

alternatively, $R^{16}$ and $R^{19}$ are each hydrogen; and $R^{17}$ and $R^{18}$ are taken together with the carbon atoms to which they are bound to form 4,5-([1,3]-dioxolanyl);

(d)

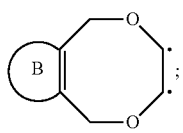

wherein

is selected from the group consisting of

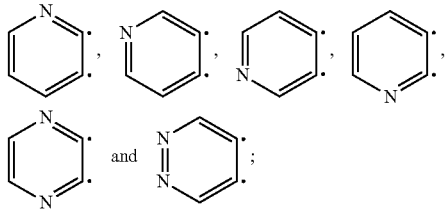

and (e)

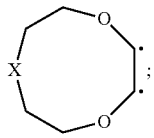

wherein X is N—$R^{20}$; and wherein $R^{20}$ is selected from the group consisting of hydrogen, phenyl, —C(O)—$C_{1-4}$alkyl, —C(O)O-t-butyl and —$SO_2$-(4-tolyl);

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the thrombin receptor (selected from the group consisting of thrombosis, restenosis, inflammation, stroke, atherosclerosis, ischemic conditions, angiogenesis and related disorders, cancer, and neurodegenerative disorders) comprising administering to a subject in need thereof comprising a therapeutically effective amount of any of the compounds or pharmaceutical compositions described above.

Another example of the invention is the use of any of the compounds described herein in the preparation of a medicament for treating: (a) thrombosis, (b) restenosis, (c) inflammation, (d) stroke, (e) atherosclerosis, (f) ischemic conditions, (g) angiogenesis or related disorder, (h) cancer, or (i) neurodegenerative disorder, in a subject in need thereof.

DETAILED DESCRIPTION OF THE INVENTION

The present invention is directed to a process for the preparation of compound of formula (I)

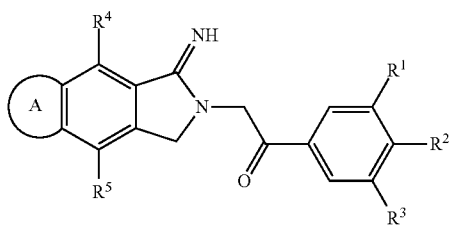

wherein $R^1$, $R^2$, $R^3$ $R^4$, $R^5$ and

are as herein defined. The compounds of the present invention are thrombin antagonists, useful in the treatment of thrombosis, restenosis, inflammation, stroke, atherosclerosis, ischemic conditions, angiogensis and related disorders, cancer, and neurodegenerative disorders. In an embodiment, the compounds of the present invention are useful for the treatment of a disorder selected from the group consisting of thrombosis, restenosis, atherosclerosis and inflammation.

In an embodiment, the present invention is directed to compounds of formula (I) wherein $R^1$ is $C_{3-5}$alkyl. In another embodiment, the present invention is directed to compounds of formula (I) wherein $R^1$ is $C_4$alkyl. In another embodiment, the present invention is directed to compounds of formula (I) wherein $R^1$ is t-butyl.

In an embodiment, the present invention is directed to compounds of formula (I) wherein $R^2$ is selected from the group consisting of hydroxy and $C_{1-2}$alkoxy. In another embodiment, the present invention is directed to compounds of formula (I) wherein $R^2$ is selected from the group consisting of hydroxy and methoxy.

In an embodiment, the present invention is directed to compounds of formula (I) wherein $R^3$ is selected from the group consisting of hydrogen, halogen, $C_{3-6}$alkyl, 1-piperidinyl, 1-piperazinyl and 4-morpholinyl; wherein the 1-piperidinyl, 1-piperazinyl or 4-morpholinyl is optionally substituted with a substituent selected from the group consisting of $C_{1-4}$alkyl. In another embodiment, the present invention is directed to compounds of formula (I) wherein $R^3$ is selected from the group consisting of hydrogen, halogen, $C_{3-6}$alkyl, 1-piperazinyl and 4-morpholinyl; wherein the 1-piperazinyl is optionally substituted with a substituent selected from the group consisting of $C_{1-4}$alkyl.

In another embodiment, the present invention is directed to compounds of formula (I) wherein $R^3$ is selected from the group consisting of hydrogen, bromo, t-butyl, 4-morpholinyl and 1-(4-methyl-piperazinyl). In another embodiment, the present invention is directed to compounds of formula (I) wherein $R^3$ is selected from the group consisting of hydrogen, t-butyl, 4-morpholinyl and 1-(4-methyl-piperazinyl). In another embodiment, the present invention is directed to compounds of formula (I) wherein $R^3$ is selected from the group consisting of t-butyl, 4-morpholinyl and 1-(4-methyl-piperazinyl). In another embodiment, the present invention is directed to compounds of formula (I) wherein $R^3$ is selected from the group consisting of t-butyl and 4-morpholinyl.

In an embodiment, the present invention is directed to compounds of formula (I) wherein $R^2$ and $R^3$ are taken together with the carbon atoms to which they are bound to form 2,3-morpholinyl or 2,3-(4-methyl-morpholinyl). In another embodiment, the present invention is directed to compounds of formula (I) wherein $R^2$ and $R^3$ are taken together with the carbon atoms to which they are bound to form 2,3-(4-methyl-morpholinyl).

In an embodiment, the present invention is directed to compounds of formula (I) wherein $R^4$ is selected from the group consisting of hydrogen and fluoro; and $R^5$ is selected from the group consisting of hydrogen and fluoro; provided that $R^4$ and $R^5$ are not each fluoro. In another embodiment, the present invention is directed to compounds of formula (I) wherein $R^4$ is hydrogen; and $R^5$ is hydrogen.

In an embodiment of the present invention,

is

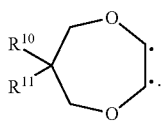

In another embodiment of the present invention,

is

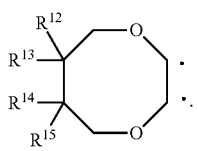

In another embodiment of the present invention,

is

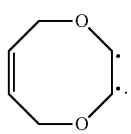

In another embodiment of the present invention,

is

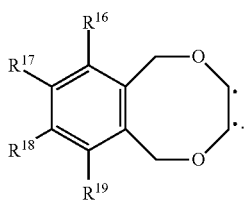

In another embodiment of the present invention, (A)

is

[structure: 8-membered ring with R²⁰—N, two O atoms]

In another embodiment of the present invention, (A)

is

[structure: B ring fused with —CH₂—O—CH₂—O— bridge];

wherein (B)

is selected from the group consisting of

[pyridine isomers], [pyridine], [pyridine], [pyridine],

[pyrazine] and [pyridazine].

In another embodiment of the present invention, (A)

is

[structure: B ring fused with —CH₂—O—CH₂—O— bridge];

wherein (B)

is selected from the group consisting of

[pyridine], [pyridine], [pyridine], [pyridine], and

[pyrazine].

In another embodiment of the present invention, (A)

is

[structure: B ring fused with —CH₂—O—CH₂—O— bridge];

wherein (B)

is selected from the group consisting of

[pyridine], [pyridine], and [pyrazine],

In another embodiment of the present invention, (A)

is

[structure: B ring fused with —CH₂—O—CH₂—O— bridge];

wherein (B)

is selected from the group consisting of

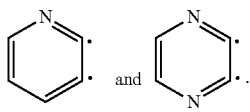 and

In an embodiment, the present invention is directed to compounds of formula (I) wherein

is (a)

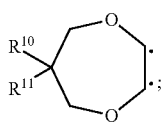

wherein $R^{10}$ is selected from the group consisting of hydrogen, halogen and $C_{1-4}$alkyl; and $R^{11}$ is selected from the group consisting of hydrogen, fluoro, $C_{1-2}$alkyl, —$CH_2$—C(O)H, —($C_{1-4}$alkyl)—OH, —$CH_2CH(OC_{1-2}$alkyl$)_2$ and —($C_{1-4}$alkyl)—$NR^AR^B$; wherein $R^A$ and $R^B$ are each independently selected from the group consisting of hydrogen and $C_{1-2}$alkyl; alternatively, $R^A$ and $R^B$ are taken together with the nitrogen atom to which they are bound to form a monocyclic nitrogen-containing heterocyclyl group; and wherein the monocyclic nitrogen-containing heterocyclyl group is optionally substituted with $C_{1-2}$alkyl.

In another embodiment, the present invention is directed to compounds of formula (I) wherein

is (a)

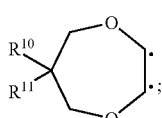

wherein $R^{10}$ is selected from the group consisting of hydrogen, halogen and $C_{1-2}$alkyl; and $R^{11}$ is selected from the group consisting of hydrogen, $C_{1-2}$alkyl, —$CH_2$—C(O)H, —($C_{1-2}$alkyl)—OH, —$CH_2$—CH(OC$_{1-2}$alkyl$)_2$ and —($C_{1-2}$alkyl)—$NR^AR^B$; wherein $R^A$ and $R^B$ are each independently selected from hydrogen or $C_{1-2}$alkyl; alternatively, $R^A$ and $R^B$ are taken together with the nitrogen atom to which they are bound to form a monocyclic nitrogen-containing heterocyclyl selected from the group consisting of morpholinyl, piperazinyl, thiazolidinyl and pyrrolidinyl; wherein the monocyclic nitrogen-containing heterocyclyl is optionally substituted with $C_{1-2}$alkyl.

In another embodiment, the present invention is directed to compounds of formula (I) wherein

is (a)

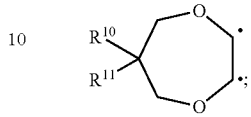

wherein $R^{10}$ is selected from the group consisting of hydrogen, fluoro and methyl; and $R^{11}$ is selected from the group consisting of hydrogen, fluoro, methyl, —$CH_2$—C(O)H, —$CH_2CH_2$—OH, —$CH_2$—CH(OCH$_2$CH$_3$)$_2$, methylamino-ethyl-, dimethylamino-ethyl-, 4-morpholinyl-ethyl-, 1-(4-methyl-piperazinyl), 2-thiazolidinyl-methyl-, 3-thiazolidinyl-ethyl- and 1-pyrrolidinyl-ethyl-.

In another embodiment, the present invention is directed to compounds of formula (I) wherein

is (a)

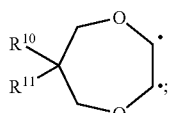

wherein $R^{10}$ is selected from the group consisting of hydrogen, fluoro and methyl; and $R^{11}$ is selected from the group consisting of hydrogen, fluoro, methyl, —$CH_2$—CH(OCH$_2$CH$_3$)$_2$, 2-thiazolidinyl-methyl- and 3-thiazolidinyl-ethyl-. In another embodiment, the present invention is directed to compounds of formula (I) wherein

is (a)

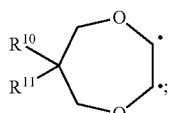

wherein $R^{10}$ is selected from the group consisting of hydrogen and methyl; and $R^{11}$ is selected from the group consisting of hydrogen, methyl, 2-thiazolidinyl-methyl- and 3-thiazolidinyl-ethyl-.

In an embodiment, the present invention is directed to compounds of formula (I) wherein

is (b)

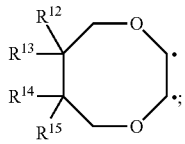

wherein $R^{12}$, $R^{13}$, $R^{14}$ and $R^{15}$ are each hydrogen or are each fluoro; alternatively, $R^{12}$ and $R^{14}$ are taken together as an electron pair to form a bond between the carbon atoms to which they are bound; and $R^{13}$ and $R^{15}$ are each hydrogen; alternatively, $R^{12}$ and $R^{14}$ are taken together as an electron pair to form a bond between the carbon atoms to which they are bound; and $R^{13}$ and $R^{15}$ are taken together with the carbon atoms to which they are bound to form a bridging group selected from the group consisting of

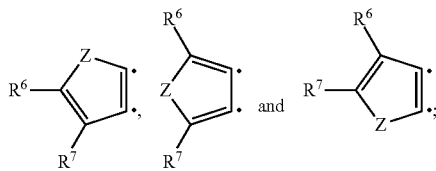

wherein Z is selected from the group consisting of S and O; and wherein $R^6$ and $R^7$ are each independently selected from the group consisting of $C_{1-2}$alkyl and —C(O)O—($C_{1-2}$alkyl).

In another embodiment, the present invention is directed to compounds of formula (I) wherein

is (b)

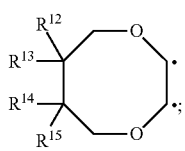

wherein $R^{12}$, $R^{13}$, $R^{14}$ and $R^{15}$ are each hydrogen or are each fluoro; alternatively, $R^{12}$ and $R^{14}$ are taken together as an electron pair to form a bond between the carbon atoms to which they are bound; and $R^{13}$ and $R^{15}$ are each hydrogen; alternatively, $R^{12}$ and $R^{14}$ are taken together as an electron pair to form a bond between the carbon atoms to which they are bound; and $R^{13}$ and $R^{15}$ are taken together with the carbon atoms to which they are bound to form a bridging group selected from the group consisting of

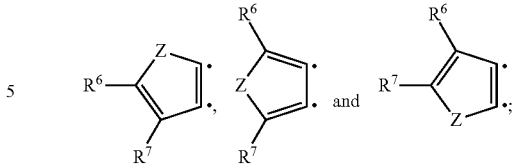

wherein Z is S; and wherein $R^6$ and $R^7$ are each independently selected from the group consisting of methyl and methoxycarbonyl-.

In another embodiment, the present invention is directed to compounds of formula (I) wherein

is (b)

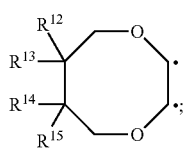

wherein $R^{12}$, $R^{13}$, $R^{14}$ and $R^{15}$ are each hydrogen or are each fluoro; alternatively, $R^{12}$ and $R^{14}$ are taken together as an electron pair to form a bond between the carbon atoms to which they are bound; and $R^{13}$ and $R^{15}$ are each hydrogen; alternatively, $R^{12}$ and $R^{14}$ are taken together as an electron pair to form a bond between the carbon atoms to which they are bound; and $R^{13}$ and $R^{15}$ are taken together with the carbon atoms to which they are bound to form a bridging group selected from the group consisting of

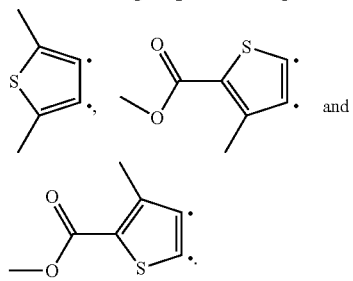

In another embodiment, the present invention is directed to compounds of formula (I) wherein

is (b)

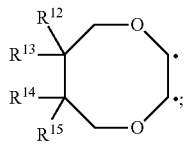

wherein $R^{12}$, $R^{13}$, $R^{14}$ and $R^{15}$ are each hydrogen or are each fluoro; alternatively, $R^{12}$ and $R^{14}$ are taken together as an electron pair to form a bond between the carbon atoms to which they are bound; and $R^{13}$ and $R^{15}$ are each hydrogen; alternatively, $R^{12}$ and $R^{14}$ are taken together as an electron pair to form a bond between the carbon atoms to which they are bound; and $R^{13}$ and $R^{15}$ are taken together with the carbon atoms to which they are bound to form a bridging group selected from the group consisting of

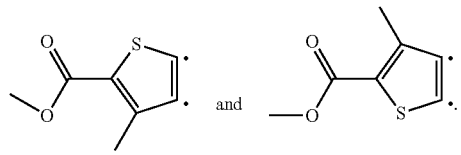

In another embodiment, the present invention is directed to compounds of formula (I) wherein

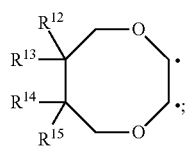

is (b)

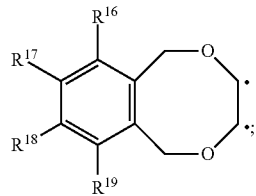

wherein $R^{12}$, $R^{13}$, $R^{14}$ and $R^{15}$ are each hydrogen; alternatively, $R^{12}$ and $R^{14}$ are taken together as an electron pair to form a bond between the carbon atoms to which they are bound; and $R^{13}$ and $R^{15}$ are each hydrogen. In another embodiment, the present invention is directed to compounds of formula (I) wherein

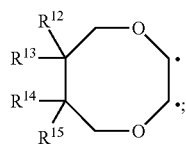

is (b)

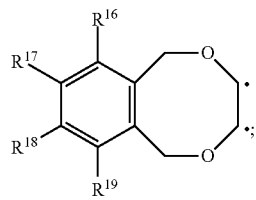

wherein $R^{12}$, $R^{13}$, $R^{14}$ and $R^{15}$ are each hydrogen.

In an embodiment, the present invention is directed to compounds of formula (I) wherein

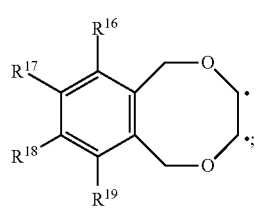

is (c)

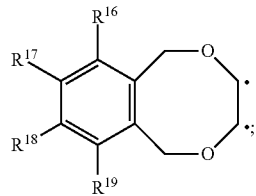

wherein $R^{16}$, $R^{17}$, $R^{18}$ and $R^{19}$ are each independently selected from the group consisting of hydrogen, halogen, nitro, $C_{1-2}$alkyl, —C(O)O—($C_{1-2}$alkyl) and —CO$_2$H; provided that at least two of $R^{16}$, $R^{17}$, $R^{18}$ and $R^{19}$ are hydrogen; alternatively, $R^{16}$ and $R^{19}$ are each hydrogen; and $R^{17}$ and $R^{18}$ are taken together with the carbon atoms to which they are bound to form 4,5-([1,3]-dioxolanyl).

In another embodiment, the present invention is directed to compounds of formula (I) wherein is (c)

wherein $R^{16}$, $R^{17}$, $R^{18}$ and $R^{19}$ are each independently selected from the group consisting of hydrogen, fluoro, nitro, methyl, methoxy-carbonyl- and carboxy; provided that at least $R^{16}$ and $R^{19}$ or $R^{17}$ and $R^{18}$ are each hydrogen; alternatively, $R^{16}$ and $R^{19}$ are each hydrogen; and $R^{17}$ and $R^{18}$ are taken together with the carbon atoms to which they are bound to form 4,5-([1,3]-dioxolanyl).

In another embodiment, the present invention is directed to compounds of formula (I) wherein is (c)

wherein $R^{16}$, $R^{17}$, $R^{18}$ and $R^{19}$ are each independently selected from the group consisting of hydrogen, fluoro, nitro, methyl, methoxy-carbonyl- and carboxy; provided that at least $R^{16}$ and $R^{19}$ or $R^{17}$ and $R^{18}$ are each hydrogen.

In another embodiment, the present invention is directed to compounds of formula (I) wherein (A)

is (c)

<chemical structure: benzene ring fused with 7-membered dioxepine ring, with R¹⁶, R¹⁷, R¹⁸, R¹⁹ substituents> wherein R¹⁶, R¹⁷, R¹⁸ and R¹⁹ are each independently selected from the group consisting of hydrogen, fluoro, nitro, methyl and methoxy-carbonyl-; provided that at least R¹⁶ and R¹⁹ or R¹⁷ and R¹⁸ are each hydrogen. In another embodiment, the present invention is directed to compounds of formula (I) wherein (A)

is (c)

<chemical structure: benzene ring fused with 7-membered dioxepine ring, with R¹⁶, R¹⁷, R¹⁸, R¹⁹ substituents>

$R^{16}$ is hydrogen; $R^{17}$ is selected from the group consisting of hydrogen, nitro and methoxy-carbonyl-; $R^{18}$ is selected from the group consisting of hydrogen and nitro; and $R^{19}$ is hydrogen; provided that one of $R^{17}$ or $R^{18}$ is hydrogen.

In an embodiment, the present invention is directed to compounds of formula (I) wherein (A)

is (d)

<chemical structure: B ring fused with 7-membered dioxepine ring> wherein (B)

is selected from the group consisting of

<chemical structures: four pyridine isomers>, and

<chemical structure: pyrazine>.

In another embodiment, the present invention is directed to compounds of formula (I) wherein (A)

is (d)

<chemical structure: B ring fused with 7-membered dioxepine ring> wherein (B)

is selected from the group consisting of

<chemical structures: two pyridines> and <chemical structure: pyrazine>.

In another embodiment, the present invention is directed to compounds of formula (I) wherein (A)

is (d)

<chemical structure: B ring fused with 7-membered dioxepine ring> wherein

is selected from the group consisting of

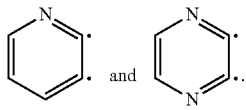

In an embodiment of the present invention,

is

In another embodiment of the present invention,

is

In another embodiment of the present invention,

is

In another embodiment of the present invention,

is

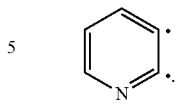

In another embodiment of the present invention,

is

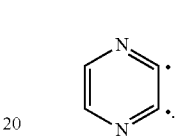

In another embodiment of the present invention,

is

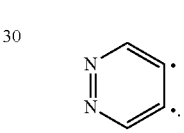

In an embodiment, the present invention is directed to compounds of formula (I) wherein

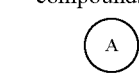

is (e)

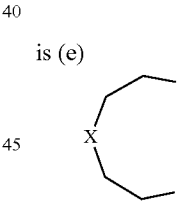

wherein X is N—$R^{20}$; and $R^{20}$ is selected from the group consisting of hydrogen, phenyl, —C(O)—($C_{1-4}$alkyl), —C(O)O-t-butyl and —$SO_2$-(4-tolyl). In another embodiment, the present invention is directed to compounds of formula (I) wherein

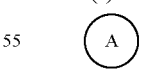

is (e)

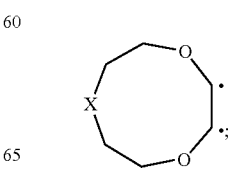

wherein X is N—R[20]; and R[20] is selected from the group consisting of hydrogen, phenyl, —C(O)-methyl, —C(O)O-t-butyl and —SO$_2$-(4-tolyl). In another embodiment, the present invention is directed to compounds of formula (I) wherein

is (e)

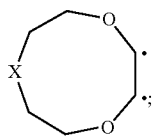

wherein X is N—R[20]; and R[20] is selected from the group consisting of —C(O)O-t-butyl and —SO$_2$-(4-tolyl).

Additional embodiments of the present invention, include those wherein the substituents selected for one or more of the variables defined herein (i.e. R[1], R[2], R[3], R[4], R[5],

etc.) are independently selected to be any individual substituent or any subset of substituents selected from the complete list as defined herein. In another embodiment of the present invention is any single compound or subset of compounds selected from the representative compounds listed in Tables 1-6 below.

Representative compounds of the present invention are as listed in Table 1 to 6, below.

TABLE 1

Representative Compounds of Formula (I)

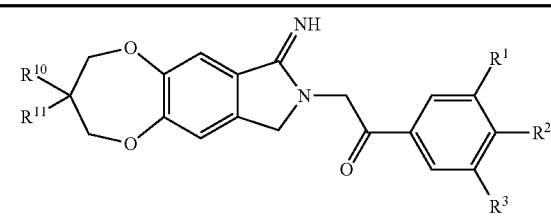

| ID No. | R[10] | R[11] | R[1] | R[2] | R[3] |
|---|---|---|---|---|---|
| 4 | H | H | t-butyl | hydroxy | t-butyl |
| 9 | methyl | methyl | t-butyl | hydroxy | t-butyl |
| 12 | H | 4-morpholinyl-ethyl- | t-butyl | hydroxy | t-butyl |
| 13 | H | 1-pyrrolidinyl-ethyl- | t-butyl | hydroxy | t-butyl |
| 14 | H | —CH$_2$—C(O)H | t-butyl | hydroxy | t-butyl |
| 15 | H | 1-(4-methyl-piperazinyl)-ethyl | t-butyl | hydroxy | t-butyl |
| 16 | H | dimethyl-amino-ethyl- | t-butyl | hydroxy | t-butyl |
| 17 | H | 1-(2-hydroxy-ethyl) | t-butyl | hydroxy | t-butyl |
| 37 | H | methyl-amino-ethyl- | t-butyl | hydroxy | t-butyl |
| 43 | H | 4-morpholinyl-ethyl- | t-butyl | methoxy | 4-morpholinyl |
| 44 | H | 2-thiazolidinyl-methyl | t-butyl | methoxy | 4-morpholinyl |
| 45 | H | 3-thiazolidinyl-ethyl | t-butyl | methoxy | 4-morpholinyl |
| 92 | fluoro | fluoro | t-butyl | methoxy | 4-morpholinyl |
| 93 | fluoro | fluoro | t-butyl | hydroxy | t-butyl |

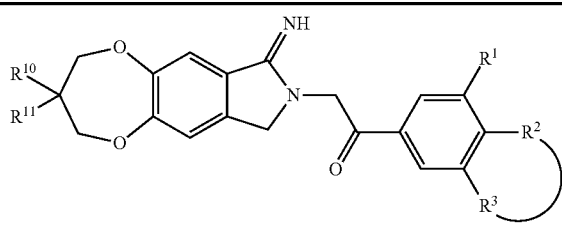

| ID No. | R[10] | R[11] | R[1] | R[2] + R[3] taken together with C atoms |
|---|---|---|---|---|
| 19 | H | H | t-butyl | 2,3-(4-methyl-morpholinyl) |
| 20 | H | 1-(2,2-diethoxy)-ethyl- | t-butyl | 2,3-(4-methyl-morpholinyl) |
| 21 | H | 4-morpholinyl-ethyl- | t-butyl | 2,3-(4-methyl-morpholinyl) |
| 24 | H | 1-pyrrolidinyl-ethyl- | t-butyl | 2,3-(4-methyl-morpholinyl) |

TABLE 1-continued

Representative Compounds of Formula (I)

| | | | | |
|---|---|---|---|---|
| 25 | H | 1-(2-hydroxy-ethyl) | t-butyl | 2,3-(4-methyl-morpholinyl) |
| 26 | H | 4-methyl-piperazinyl-ethyl- | t-butyl | 2,3-(4-methyl-morpholinyl) |
| 27 | H | 3-thiazolidinyl-ethyl | t-butyl | 2,3-(4-methyl-morpholinyl) |
| 32 | H | dimethyl-amino-ethyl- | t-butyl | 2,3-(4-methyl-morpholinyl) |
| 36 | H | H | t-butyl | 2,3-morpholinyl |

TABLE 2

Representative Compounds of Formula (I)

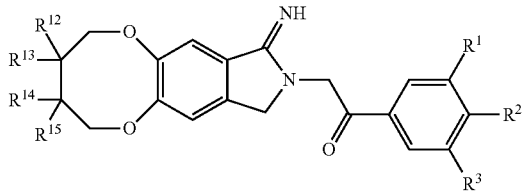

| ID No. | $R^{12}, R^{13}, R^{14}, R^{15}$ | $R^1$ | $R^2$ | $R^3$ |
|---|---|---|---|---|
| 5 | H, H, H, H | t-butyl | hydroxy | t-butyl |
| 90 | F, F, F, F | t-butyl | methoxy | 4-morpholinyl |
| 91 | F, F, F, F | t-butyl | hydroxy | t-butyl |

| ID | $R^{12}, R^{13}, R^{14}, R^{15}$ | $R^1$ | $R^2 + R^3$ taken together with C atoms |
|---|---|---|---|
| 18 | H, H, H, H | t-butyl | 2,3-(4-methyl-morpholinyl) |

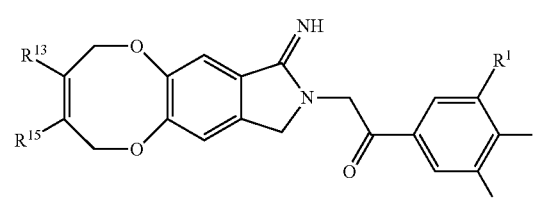

| ID No. | $R^1$ | $R^2$ | $R^3$ |
|---|---|---|---|
| 97 | t-butyl | methoxy | 4-morpholinyl |
| 100 | t-butyl | hydroxy | t-butyl |

TABLE 3

Representative Compounds of Formula (I)

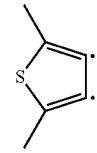

| ID No. | $R^{13} + R^{15}$ taken together with C atoms | $R^1$ | $R^2$ | $R^3$ |
|---|---|---|---|---|
| 74 | 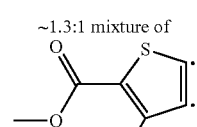 | t-butyl | hydroxy | t-butyl |
| 101 | ~1.3:1 mixture of 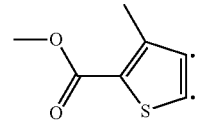 and | t-butyl | hydroxy | t-butyl |

TABLE 4

Representative Compounds of Formula (I)

| ID No. | $R^{17}$ | $R^{18}$ | $R^1$ | $R^2$ | $R^3$ |
|---|---|---|---|---|---|
| 46 | H | H | t-butyl | methoxy | 4-morpholinyl |
| 47 | H | H | t-butyl | hydroxy | t-butyl |
| 53 | methoxy-carbonyl- | H | t-butyl | methoxy | bromo |

TABLE 4-continued

Representative Compounds of Formula (I)

| ID | R¹⁷ | R¹⁸ | R¹ | R² | R³ |
|---|---|---|---|---|---|
| 55 | methoxy-carbonyl- | H | t-butyl | hydroxy | t-butyl |
| 72 | carboxy | H | t-butyl | hydroxy | t-butyl |
| 73 | methoxy-carbonyl- | H | t-butyl | methoxy | 4-morpholinyl |
| 80 | H | methoxy-carbonyl- | t-butyl | hydroxy | t-butyl |
| 81 | H | carboxy- | t-butyl | hydroxy | t-butyl |
| 84 | nitro | H | t-butyl | hydroxy | t-butyl |
| mixture of | H | nitro | t-butyl | hydroxy | t-butyl |
| 85 | fluoro | fluoro | t-butyl | hydroxy | t-butyl |
| 89 | fluoro | fluoro | t-butyl | methoxy | 4-morpholinyl |
| 98 | methyl | methyl | t-butyl | methoxy | 4-morpholinyl |
| 99 | methyl | methyl | t-butyl | hydroxy | t-butyl |
| 102 | methoxy-carbonyl- | methoxy-carbonyl- | t-butyl | hydroxy | t-butyl |
| 103 | methoxy-carbonyl- | methoxy-carbonyl- | t-butyl | methoxy | 4-morpholinyl |
| 104 | nitro | H | t-butyl | methoxy | 4-morpholinyl |
| mixture of | H | nitro | t-butyl | methoxy | 4-morpholinyl |

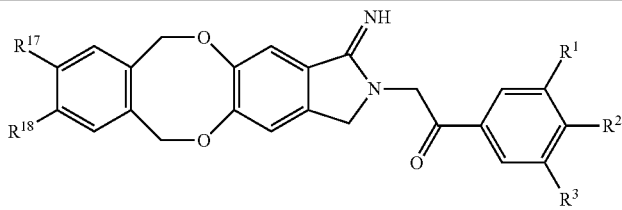

| ID No. | R¹⁷ + R¹⁸ taken together with C atoms | R¹ | R² | R³ |
|---|---|---|---|---|
| 59 | (4,5-([1,3]-dioxolanyl) | t-butyl | methoxy | 4-morpholinyl |

| ID No. | R¹⁶ | R¹⁹ | R¹ | R² | R³ |
|---|---|---|---|---|---|
| 87 | fluoro | fluoro | t-butyl | hydroxy | t-butyl |
| 88 | fluoro | fluoro | t-butyl | methoxy | 4-morpholinyl |

TABLE 5

Representative Compounds of Formula (I)

| ID No. | R¹ | R² | R³ |
|---|---|---|---|
| 49 | t-butyl | hydroxy | t-butyl |
| 52 | t-butyl | methoxy | 4-morpholinyl |
| 54 | t-butyl | methoxy | bromo |
| 75 | t-butyl | methoxy | t-butyl |
| 82 | t-butyl | hydroxy | H |

| ID No. | R¹ | R² + R³ taken together with C atoms |
|---|---|---|
| 70 | t-butyl | 2,3-(4-methyl-morpholinyl) |

TABLE 5-continued

Representative Compounds of Formula (I)

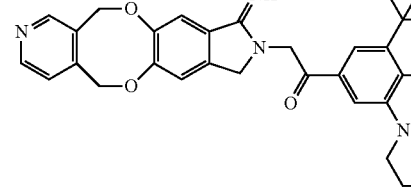

| ID No. | R¹ | R² | R³ |
|---|---|---|---|
| 48 | t-butyl | hydroxy | t-butyl |
| 51 | t-butyl | methoxy | 4-morpholinyl |
| 71 | t-butyl | methoxy | 1-(4-methyl-piperazinyl) |
| 76 | t-butyl | methoxy | t-butyl |
| 83 | t-butyl | hydroxy | H |

| ID | R¹ | R² + R³ taken together with C atoms |
|---|---|---|
| 69 | t-butyl | 2,3-(4-methyl-morpholinyl) |

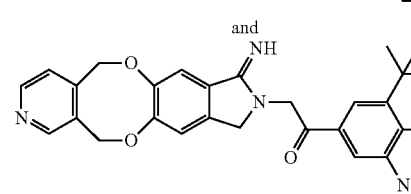

| ID No. | R¹ | R² | R³ |
|---|---|---|---|
| 58 | t-butyl | methoxy | 4-morpholinyl |
| 77 | t-butyl | hydroxy | t-butyl |

| ID No. | R¹ | R² + R³ taken together with C atoms |
|---|---|---|
| 60 | t-butyl | 2,3-(4-methyl-morpholinyl) |

TABLE 6

Representative Compounds of Formula (I)

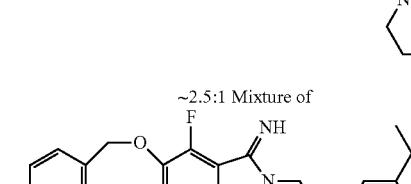

| ID No. | X | R¹ | R² | R³ |
|---|---|---|---|---|
| 10 | N—C(O)O-t-butyl | t-butyl | hydroxy | t-butyl |
| 11 | NH | t-butyl | hydroxy | t-butyl |
| 41 | N—C(O)O-t-butyl | t-butyl | methoxy | 4-morpholinyl |
| 42 | NH | t-butyl | methoxy | 4-morpholinyl |
| 63 | N—SO₂-(4-tolyl) | t-butyl | methoxy | 4-morpholinyl |
| 67 | N—C(O)—CH₃ | t-butyl | methoxy | 4-morpholinyl |
| 68 | N-phenyl | t-butyl | methoxy | 4-morpholinyl |

Additional representative compounds of the present invention, prepared and tested as a mixture of synthesis regionisomers are as listed in Table 7, below.

TABLE 7

Representative Compounds of Formula (I)

| ID No. | Structure |
|---|---|
| 61 | Mixture of 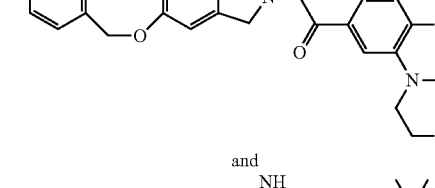 |
| 94 | ~2.5:1 Mixture of 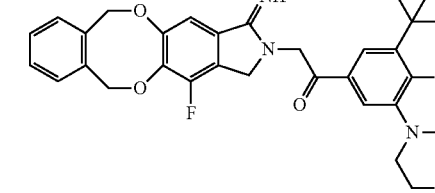 |
| 96 | Tentatively Assigned as |

In another embodiment, the present invention is directed to compounds of formula (I) whose IC$_{50}$, measured according to the procedure described in Biological Example 1, is less than or equal to about 1.0 μM, preferably less than or equal to about 0.50 μM, more preferably less than or equal to about 0.25 μM.

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "C$_{1-4}$alkyl" shall mean a carbon chain composition of 1-4 carbon atoms.

One skilled in the art will recognize that the terms "-(alkyl)-" and "—($C_{1-4}$alkyl)-" shall denote any alkyl or $C_{1-4}$alkyl carbon chain as herein defined, wherein said alkyl or $C_{1-4}$alkyl chain is divalent and is further bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted alkyl" shall mean alkyl group as defined above substituted with at least one hydroxy group. Preferably, the alkyl group is substituted with one hydroxy group. Preferably, the alkyl group is substituted with a hydroxy group at the terminal carbon. Suitable examples include, but are not limited to, —$CH_2(OH)$, —$CH_2$—$CH_2(OH)$, —$CH_2$—$CH(OH)$—$CH_2$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{1-4}$alkoxy" shall mean an oxygen ether radical composition of 1-4 carbon atoms.

As used herein, unless otherwise noted, the term "aryl" shall refer to unsubstituted carbocylic aromatic groups such as phenyl, naphthyl, and the like. As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, the term "monocyclic nitrogen-containing heterocyclyl" shall mean any five to eight, preferably five to six, membered aromatic, partially unsaturated or saturated ring structure containing at least one nitrogen atom. Suitably example include, pyrrolyl, oxazolyl, imidazolyl, isoxazolyl, isothiazolyl, triazolyl, thiadiazolyl, pyridyl, pyridazinyl, pyrimidinyl, pyrazinyl, pyrrolinyl, pyrrolidinyl, imidazolinyl, imidazolidinyl, pyrazolinyl, pyrazolidinyl, piperidinyl, piperazinyl, morpholinyl, thiomorpholinyl, and the like. Preferred monocyclic nitrogen-containing heterocyclyl include, but are not limited to morpholinyl, pyrrolidinyl, piperazinyl, piperidinyl and thiazolidinyl. In an embodiment, the mono-cyclic nitrogen-containing heterocyclyl is selected from the group consisting of morpholinyl, thiazolidinyl and piperazinyl.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl $C_1$-$C_6$alkylaminocarbonyl $C_1$-$C_6$alkyl" substituent refers to a group of the formula

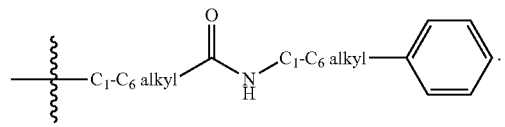

Abbreviations used in the specification, particularly the Schemes and Examples, are as follows

| | |
|---|---|
| Boc or BOC or t-Boc = | tert-Butoxy-carbonyl- |
| BSA = | Bovine serum albumin |
| CGS Buffer = | Citrate-glucose-sodium chloride buffer |
| DCM = | Dichloromethane |
| DDQ = | 2,3-Dichloro-5,6-dicyano-1,4-benzoquinone |
| DEAD = | Diethylazodicarboxylate |
| DIPEA or DIEA = | Diisopropylethylamine |
| DMF = | N,N-Dimethylformamide |
| DMSO = | Dimethylsulfoxide |
| DPBS = | Dulbecco's Phosphate Buffered Saline |
| EA or EtOAc = | Ethyl acetate |
| EGTA = | Ethylene glycol tetracetic acid |
| EtOH = | Ethanol |
| Grubb's Catalyst = | Bis(tricyclohexylphosphine)-benzylidene-utherium (IV) dichloride |
| GPRP = | gly-Pro-Arg-Pro peptide |
| Har = | Ser-pFPhe-Har-Leu-Har-Lys-Tyr-$NH_2$ |
| HEPES = | 4-(2-Hydroxyethyl)-1-piperazine ethane sulfonic acid |
| Hex = | Hexanes |
| HOAc = | Acetic acid |
| HPLC = | High pressure liquid chromatography |
| MeOH = | Methanol |
| Mesyl = | Methylsulfonyl |
| $NaBH(OAc)_3$ = | Sodium triacetoxyborohydride |

| | |
|---|---|
| NMP = | N-methyl-2-pyrrolidinone |
| Pd-C = | Palladium on carbon catalyst |
| $Pd_2(OAc)_2$ = | Palladium(II)acetate |
| $Pd(PPh_3)_2Cl_2$ = | Bis(triphenylphosphine)palladium (II) chloride |
| $PPh_3$ = | Triphenylphosine |
| PPP = | Platelet poor plasma |
| PRP = | Platelet rich lasma |
| RANEY ® nickel = | Nickel aluminum solid catalyst |
| TEA = | Triethylamine |
| TFA = | Trifluoroacetic acid |
| THF = | Tetrahydrofuran |
| Tosyl = | p-Toluenesulfonyl |

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, 1,2-dichloroethane, dichloromethane, methyl t-butyl ether (MTBE), toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates (containing groups of the formula —C(O)O—R wherein R is for example methyl, ethyl, t-butyl, benzyl, phenylethyl, $CH_2$=CH—$CH_2$—, and the like); amides (containing groups of the formula —C(O)—R' wherein R' is for example methyl, phenyl, trifluoromethyl, and the like); N-sulfonyl derivatives (containing groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like). Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), methoxymethyl (MOM), 2-tetrahydropyranyl (THP), and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-obs}]/[\alpha\text{-max}])\times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotine acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Compounds of formula (I) may be prepared according to the process outlined in Scheme 1.

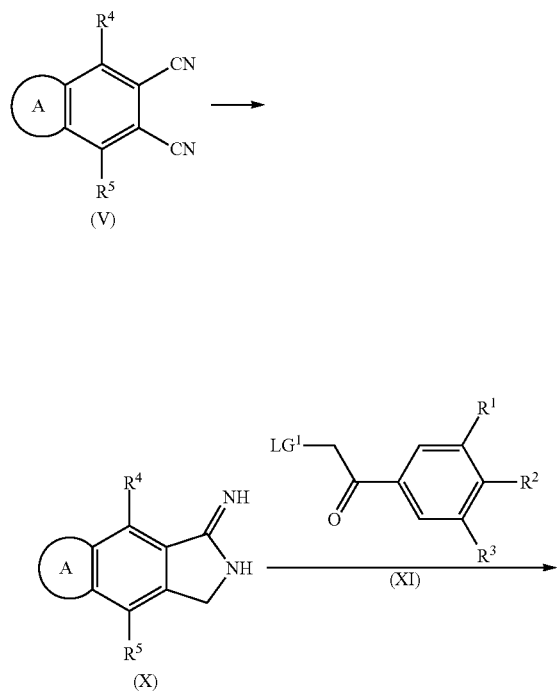

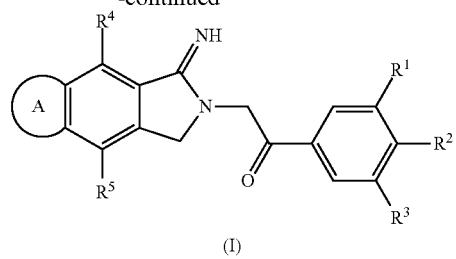

Accordingly, a suitably substituted compound of formula (V), a known compound or compound prepared by known methods, is reacted with a suitably selected reducing agent such as hydrogen gas in the presence of a catalyst such as Pt, $PtO_2$, Raney® nickel, and the like; in a suitably selected solvent such as ethanol, methanol, and the like, or a mixture of solvents such as a mixture of methanol and toluene, a mixture of ethanol and toluene, and the like; to yield the corresponding compound of formula (X).

The compound of formula (X) is reacted with a suitably substituted compound of formula (XI), wherein $LG^1$ is a suitably selected leaving group such as bromo, chloro, tosyl, mesyl, and the like, preferably bromo, a known compound or compound prepared by known methods; wherein the compound of formula (XI) is preferably present in an amount in the range of from about 1.0 to about 2.0 molar equivalents (relative to the moles of the compound of formula (X)); in the presence of a suitably selected organic base such as TEA, DIPEA, and the like; wherein the base is preferably present in an amount in the range of from about 1.0 to about 2.0 molar equivalents (relative to the moles of the compound of formula (X)); in a suitably selected aprotic organic solvent such as DMF, THF, and the like; preferably at a temperature in the range of from about 10° C. to about room temperature; to yield the corresponding compound of formula (I).

The compound of formula (X) may alternatively be prepared according to the process outlined in Scheme 2, below.

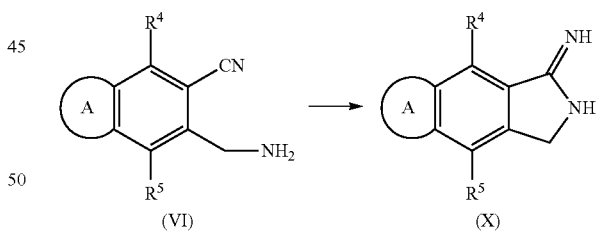

Accordingly, a suitably substituted compound of formula (VI), a known compound or compound prepared by known methods, is reacted with a suitably selected inorganic base such as $K_2CO_3$, $NaHCO_3$, $Cs_2CO_3$, and the like; in a suitably selected solvent such as methanol, ethanol, and the like; preferably at a temperature in the range of from about 20° C. to about 50° C., for example at about room temperature, in an another example at about 40° C., to yield the corresponding compound of formula (X).

Compound of formula (V) and (VI) are known compound or compound which may be prepared according to known methods. Schemes 3 through 8 which follow herein described methods for the preparation of representative compounds of formula (V) and/or (VI). Additionally, the Examples which follow herein, further describe methods for the preparation of representative compounds of formula (V) and (VI).

Compounds of formula (V) wherein

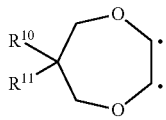

is

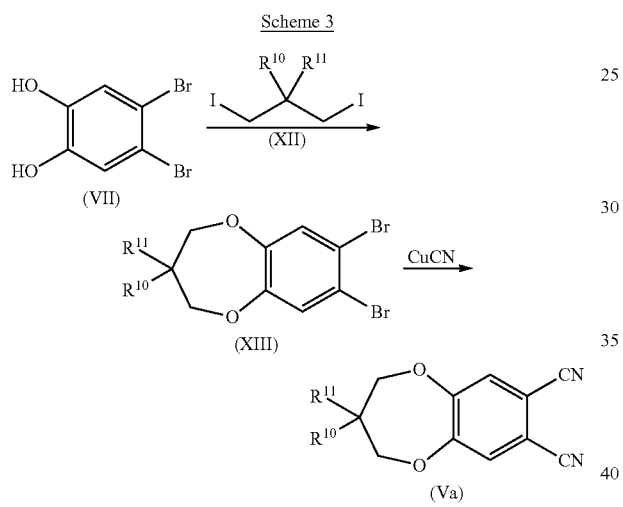

may be prepared, for example, according to the process outlined in Scheme 3, below.

Accordingly, a suitably substituted compound of formula (VII), a known compound or compound prepared by known methods, is reacted with a suitably substituted compound of formula (XII), a known compound or compound prepared by known methods; in the presence of a suitably selected inorganic base such as $K_2CO_3$, $NaHCO_3$, $Na_2CO_3$, and the like, in a suitably selected aprotic organic solvent such as DMF, NMP, and the like; to yield the corresponding compound of formula (XIII).

The compound of formula (XIII) is reacted with CuCN, a known compound, in a suitably selected aprotic organic solvent DMF, NMP, and the like, to yield the corresponding compound of formula (Va). One skilled in the art will recognize that the compound of formula (Va) may be further reacted as describe in Scheme 1 above, to yield the corresponding compound of formula (I).

Compounds of formula (V) wherein

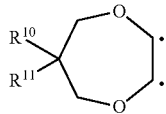

is

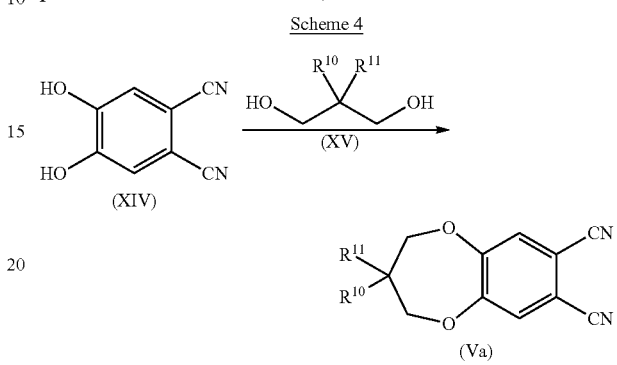

may alternatively be prepared, for example, according to the process outlined in Scheme 4, below.

Accordingly, a suitably substituted compound of formula (XIV), a known compound or compound prepared by known methods, is reacted with a suitably substituted compound of formula (XV), a known compound or compound prepared by known methods, under Mitsunobu conditions (e.g. in the presence of a suitably selected coupling system such as a mixture of $PPh_3$ and DEAD, in a suitably selected solvent such as THF); to yield the corresponding compound of formula (Va).

Compounds of formula (V) wherein

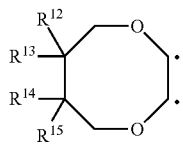

is

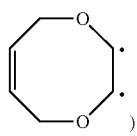

(including compounds of formula (V) wherein

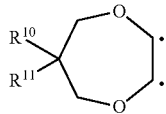

is

)

may be prepared according, for example, according to the process outlined in Scheme 5 below.

Scheme 5

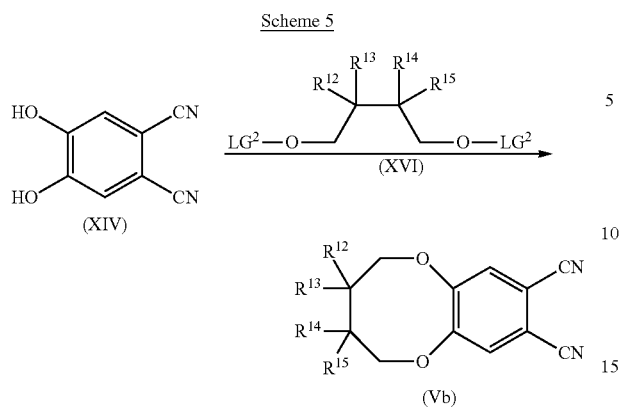

Accordingly, a suitably substituted compound of formula (XIV), a known compound or compound prepared by known methods, is reacted with a suitably substituted compound of formula (XVI), wherein $LG^2$ is a suitably selected leaving group such as mesyl, tosyl, triflyl (i.e. $-SO_2-CF_3$), and the like, preferably triflyl (i.e. $-SO_2-CF_3$), a known compound or compound prepared by known methods, in the presence of a suitably selected inorganic base such as $Cs_2CO_3$, $K_2CO_3$, $NaHCO_3$, $Na_2CO_3$, and the like, in a suitably selected aprotic organic solvent DMF, NMP, and the like, to yield the corresponding compound of formula (Vb).

Compounds of formula (V) wherein

is

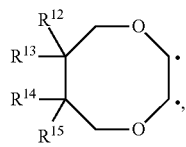

wherein $R^{13}$ and $R^{15}$ are each hydrogen and wherein $R^{12}$ and $R^{14}$ are taken together as an electron to form a bond between the carbon atoms to which they are bound to form a double bond (i.e. 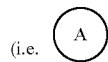

is

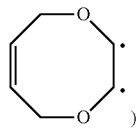 )

may alternatively be prepared according to the process outlined in Scheme 6 below.

Scheme 6

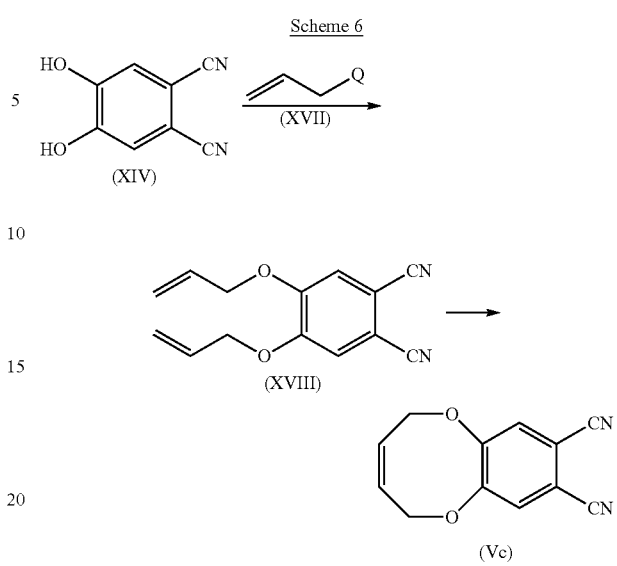

Accordingly, a suitably substituted compound of formula (XIV), a known compound or compound prepared by known methods is reacted with a suitably substituted compound of formula (XVII), wherein Q is bromo or chloro, preferably bromo, a known compound or compound prepared by known methods, in the presence of a suitably selected inorganic base such as $Cs_2CO_3$, $K_2CO_3$, $NaHCO_3$, $Na_2CO_3$, and the like, in a suitably selected aprotic organic solvent DMF, NMP, and the like, preferably at about room temperature, to yield the corresponding compound of formula (XVIII).

The compound of formula (XVIII) is reacted under ring closing metathesis conditions, in the presence of a suitably selected catalyst such as Grubb's catalyst, or a suitably selected palladium catalyst such as $Pd(PPh_3)_2Cl_2$, $Pd(OAc)_2Cl_2$, and the like; in a suitably selected aprotic organic solvent DMF, NMP, and the like, preferably at about room temperature, to yield the corresponding compound of formula (Vc).

Compounds of formula (V) wherein

is

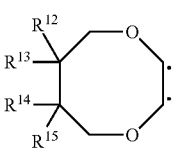

and wherein $R^{12}$ and $R^{14}$ are taken together as an electron pair to form a bond between the carbon atoms to which they are bound to form a double bond and wherein $R^{13}$ and $R^{15}$ are taken together with the carbon atoms to which they are bound to form a bridging group selected from the group consisting of

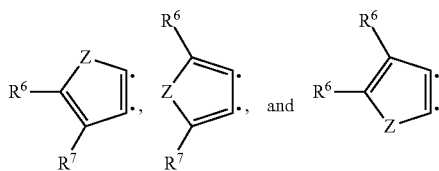

may be similarly prepared according to the process as outlined in Scheme 5 above, by substituting a suitably substituted compound of formula (XIX),

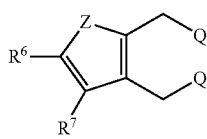

(XIX)

wherein Q is bromo or chloro, preferably bromo, or a suitably substituted compound of formula (XX)

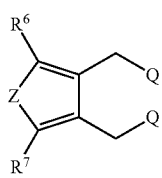

(XX)

wherein Q is bromo or chloro, preferably bromo, or a suitably substituted compound of formula (XXI)

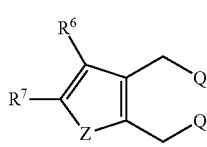

(XXI)

Q is bromo or chloro, preferably bromo, for the compound of formula (XVI), respectively.

Compounds of formula (V)

is

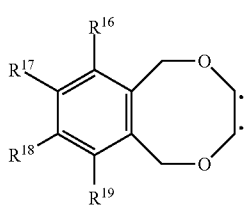

may be prepared according to the process outlined in Scheme 7 below.

Scheme 7

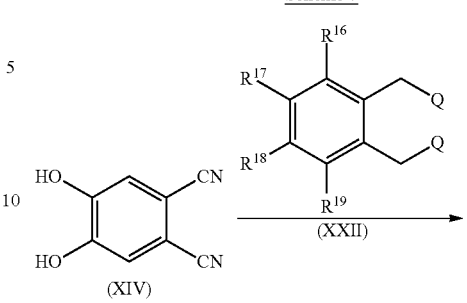

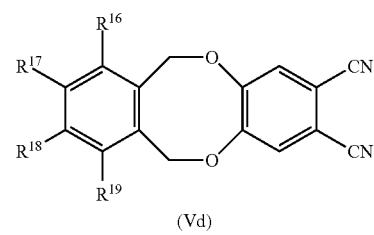

Accordingly, a suitably substituted compound of formula (XIV), a known compound or compound prepared by known methods, is reacted with a suitably substituted compound of formula of formula (XXII), Q is bromo or chloro, preferably bromo, a known compound or compound prepared by known methods, in the presence of a suitably selected inorganic base such as $K_2CO_3$, $NaHCO_3$, $Na_2CO_3$, and the like, in a suitably selected aprotic organic solvent such as DMF, NMP, and the like, to yield the corresponding compound of formula (Vd).

Compounds of formula (V) wherein

is

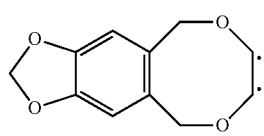

may be similarly prepared according to the process outlined in Scheme 6 above by substituting a compound of formula (XXIII)

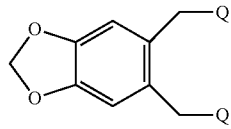

(XXIII)

wherein Q is bromo or chloro, preferably bromo, for the compound of formula (XXII).

Compounds of formula (V) wherein

is

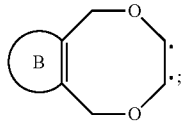

wherein

is selected from the group consisting of

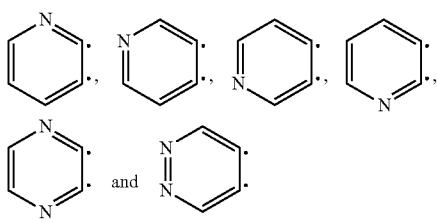

may be prepared according to the process outlined in Scheme 8, below.

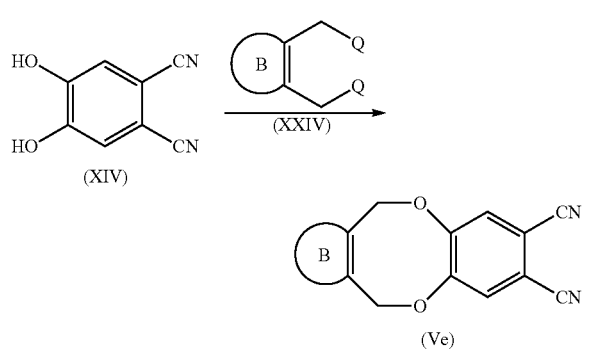

Accordingly, a suitably substituted compound of formula (XIV), a known compound or compound prepared by known methods, is reacted with a suitably substituted compound of formula of formula (XXIV), Q is bromo or chloro, preferably bromo, a known compound or compound prepared by known methods, in the presence of a suitably selected inorganic base such as $K_2CO_3$, $NaHCO_3$, $Na_2CO_3$, and the like, in a suitably selected aprotic organic solvent such as DMF, NMP, and the like, to yield the corresponding compound of formula (Ve).

Compounds of formula (V) wherein

is

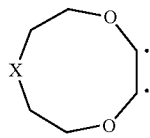

may be prepared according to the processes as outlined in Scheme 9, below.

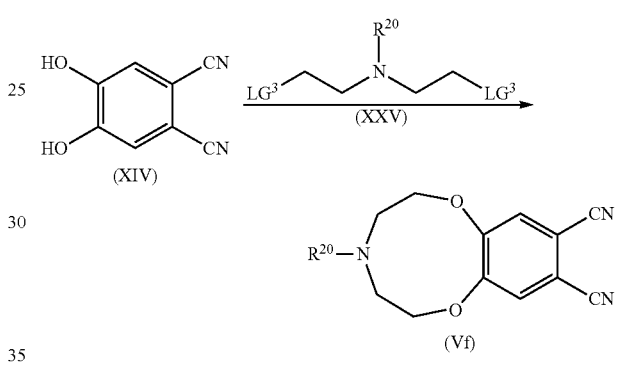

Accordingly, a suitably substituted compound of formula (XIV), a known compound or compound prepared by known methods, is reacted with a suitably substituted compound of formula (XXVI), wherein each $LG^3$ is a suitably selected leaving group such as OH, Br, I, tosyl-O—, mesyl-O—, and the like, a known compound or compound prepared by known methods in the presence of a suitably selected inorganic base such as $K_2CO_3$, $NaHCO_3$, $Na_2CO_3$, and the like, in a suitably selected aprotic organic solvent such as DMF, NMP, and the like, to yield the corresponding compound of formula (Vf).

One skilled in the art will recognize that in the process as outlined in Scheme 9 above, in the compound of formula (XXV), the $R^{20}$ group may alternatively be substituted with a suitably selected nitrogen protecting group, such as BOC, tosyl, and the like, to yield the corresponding compound of formula (Vg)

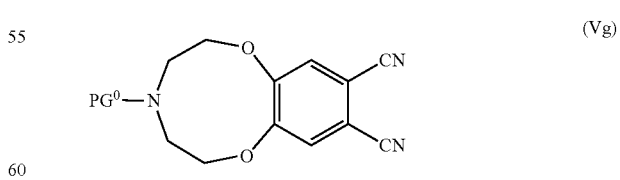

which compound may then be de-protected according to known methods, and then further reacted according to known methods to functionalize the nitrogen with a desired $R^{20}$ group.

One skilled in the art will recognize that compounds of formula (VI) may be similarly prepared according to the processes described in Scheme 3 through 8 above, by substituting a suitably substituted compound of formula (XXVII)

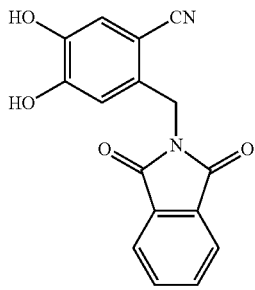

(XXVII)

for the compound of formula (XIV), to yield the corresponding compound of formula (XXVIII),

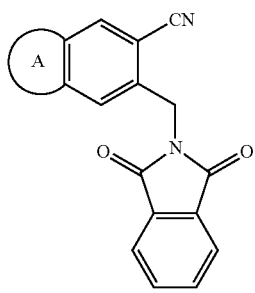

(XXVIII)

which compound of formula (XXVIII) is then de-protected according to known methods, to yield the corresponding compound of formula (VI).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1000 mg or any amount or range therein, and may be given at a dosage of from about 0.01 to about 300 mg/kg/day, or any amount or range therein, preferably from about 0.05 to about 50 mg/kg/day, or any amount or range therein, preferably from about 0.1 to about 20 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating thrombin PAR-1 receptor modulated disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably about 10 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like.

For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders of mediated by the PAR-1 thrombin receptor is required.

The daily dosage of the products may be varied over a wide range from about 0.01 to about 5000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.05 to about 50.0 mg/kg of body weight per day, or any amount or range therein. More preferably, from about 0.1 to about 20 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

INTERMEDIATE EXAMPLE 1

1,2-(1,3-Dioxo-1,3-dihydro-isoindol-2-ylmethyl)-4,5-dihydroxy-benzonitrile

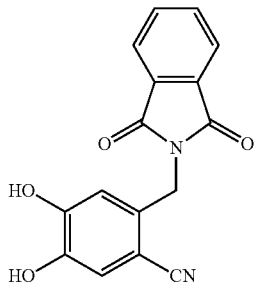 [SMILES: N#Cc1cc(O)c(O)cc1CN1C(=O)c2ccccc2C1=O]

Step A:

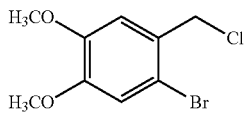

(2-Bromo-4,5-dimethoxy-phenyl)-methanol (25.09 g, 0.1015 mol) was added as a solid to a vigorously stirred solution of concentrated aqueous HCl (75 mL). The resulting white suspension was stirred at room temperature for 30 min. The resulting mixture was then extracted with CH$_2$Cl$_2$ (3×) and the combined extracts dried over MgSO$_4$, filtered and concentrated in vacuo to yield 1-bromo-2-chloromethyl-4,5-dimethoxy-benzene as a white solid.
Step B:

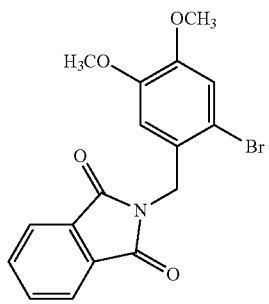 [SMILES: COc1cc(Br)c(CN2C(=O)c3ccccc3C2=O)cc1OC]

A solution of 1-bromo-2-chloromethyl-4,5-dimethoxy-benzene (26.01 g, 0.09796 mol) in dry DMF (100 mL) was treated with potassium phthalimide (19.05 g, 0.1029 mol). The resulting slurry was heated to 80° C. while stirring under nitrogen for 4.5 h. The resulting mixture was then cooled to room temperature and allowed to stir 16 h. The resulting mixture solidified, was diluted with water (400 mL) and stirred 1 h. The resulting white precipitate was collected via filtration and washed with water (1 L). The white solid was dissolved in boiling methanol (2 L). The resulting solution was reduced to about 1 L, at which time a precipitate began to form. The resulting slurry was allowed to cool to room temperature then placed on an ice bath. The precipitate was collected via filtration to yield 2-(2-bromo-4,5-dimethoxy-benzyl)-isoindole-1,3-dione as a white solid.

Step C:

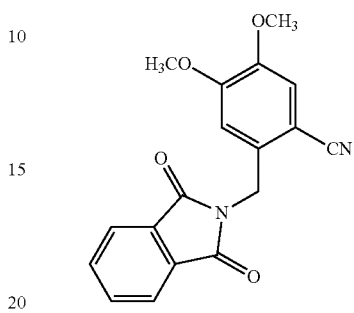

A mixture of 2-(2-bromo-4,5-dimethoxy-benzyl)isoindole-1,3-dione (26.63 g, 0.07079 mol) and copper (I) cyanide (12.7 g, 0.1416 mol) in N-methyl-2-pyrrolidinone (266 mL) was heated to reflux for 18 h under nitrogen. The resulting mixture was concentrated in vacuo and the resulting residue stirred with a mixture of chloroform (250 mL) and water (250 mL) for 30 min. The resulting suspension was filtered through CELITE and the layers separated. The organic layer was extracted with brine (2×), dried over MgSO$_4$, filtered and concentrated in vacuo. The resulting solid was crystallized from methylene chloride/methanol (500 mL) to yield 2-(1,3-dioxo-1,3-dihydro-isoindol-2-ylmethyl)-4,5-dimethoxy-benzonitrile as a white solid.

Step D:

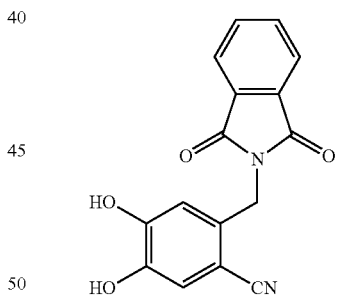

2-(1,3-dioxo-1,3-dihydro-isoindol-2-ylmethyl)-4,5-dimethoxy-benzonitrile (20.36 g, 0.0632 mol) was dissolved in warm methylene chloride (253 mL) then cooled to 0° C. Boron tribromide (1 M in CH$_2$Cl$_2$, 253 mL, 0.2527 mol) was added dropwise over 45 min while maintaining the temperature under 5° C., under nitrogen. The resulting mixture was allowed to warm to room temperature with stirring under nitrogen for 23 h. The resulting mixture was then cooled to 0° C. and quenched by the dropwise addition of methanol (90 mL) over 45 min. The resulting mixture was concentrated in vacuo. The resulting precipitate was suspended in methanol (2×) and concentrated in vacuo. The resulting precipitate was taken up in boiling methanol (900 mL) and hot filtered. The filtrate was concentrated to about 200 mL and allowed to crystallize. The resulting precipitate was collected via filtration to yield the title compound-2-(1,3-dioxo-1,3-dihydro-isoindol-2-ylmethyl)-4,5-dihydroxy-benzonitrile—as a gray solid.

EXAMPLE 1

1-(3,5-di-tert-butyl-4-hydroxyphenyl)-2-(7-imino-3,4-dihydro-[1,4]dioxepino[2,3-f]isoindol-8(2H,7H,9H)-yl)ethanone Compound #4

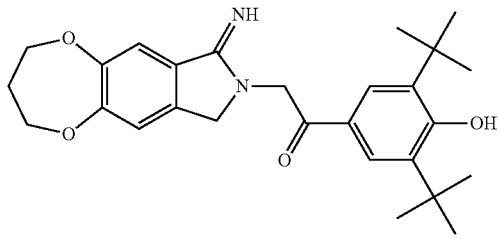 [SMILES: CC(C)(C)c1cc(C(=O)CN2Cc3cc4c(cc3C2=N)OCCCO4)cc(C(C)(C)C)c1O]

Step A:

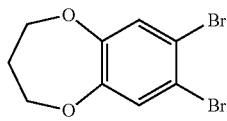 [SMILES: Brc1cc2c(cc1Br)OCCCO2]

4,5-Dibromocatechol (2.66 g, 10.0 mmol) in DMF (100 mL) was cooled in an ice bath and potassium carbonate (2.76 g, 20 mmol) was added, followed by 1,3 diiodopropane (2.96 g, 10.0 mmol) and the resulting mixture was stirred at ambient temp for 16 h. The resulting solids were filtered and the filtrate was evaporated in vacuo to yield an oil, which was partitioned between 0.1 N NaOH and chloroform. The organic layer was washed once with 0.1 N NaOH, twice with water, dried (Na$_2$SO$_4$) and evaporated in vacuo to yield a solid. This solid was triturated with methanol (20 mL) and a tan solid of 7,8-dibromo-3,4-dihydro-2H-benzo[b][1,4]dioxepine was filtered. $^1$H NMR (CDCl$_3$) δ 7.25 (s, 2H), 4.20 (m, 4H), 2.20 (m, 2H).

Step B:

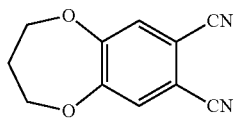 [SMILES: N#Cc1cc2c(cc1C#N)OCCCO2]

The tan solid (0.96 g, 3.1 mmol) in DMF (15 mL) and pyridine (0.75 mL) was combined with copper(I) cyanide (1.2 g, 13.3 mmol) and refluxed for 6 h. The resulting mixture was then cooled to room temperature and evaporated in vacuo to yield a solid, which was triturated three times with DCM/MeOH (30 mL). These organic extracts were combined and evaporated in vacuo to yield 3,4-dihydro-2H-benzo[b][1,4]dioxepine-7,8-dicarbonitrile (1.5 g) as a residue, which was purified via flash column chromatography (EA/Hex 2:3) to yield a white solid. $^1$H NMR (CDCl$_3$) δ 7.31 (s, 2H), 4.40 (t, J=6 Hz, 4H), 2.31 (m, 2H).

Step C:

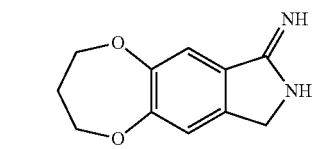 [SMILES: N=C1NCc2cc3c(cc21)OCCCO3]

The white solid (170 mg, 0.85 mmol) was semi-dissolved in absolute ethanol (20 mL) with PtO$_2$ (40 mg) and shaken on a Parr shaker under 35 psi of hydrogen at room temperature for 24 h. The resulting solution was filtered through dicalite and the filtrate was evaporated in vacuo to yield a light green solid, which was dissolved in CHCl$_3$/CH$_3$OH (40:1), dried (Na$_2$SO$_4$) and evaporated in vacuo to yield 3,4,8,9-tetrahydro-[1,4]dioxepino[2,3-f]isoindol-7(2H)-imine as a solid. $^1$H NMR (CDCl$_3$) δ 7.11 (s, 1H), 7.05 (s, 1H), 4.50 (s, 2H), 4.20 (m, 4 H), 3.5 (bs, 2H), 2.23 (m, 2H).

Step D:

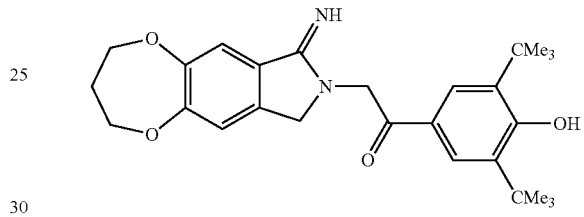

The solid (140 mg, 0.70 mmol) in DMF (7 mL) was combined with 2-bromo-1-[3,5-di(tert-butyl)-4-hydroxyphenyl]ethan-1-one (230 mg, 0.70 mmol) and stirred at room temperature for 40 h. The resulting mixture was evaporated in vacuo to yield an oil, which was purified via reverse phase HPLC to yield the title compound as a white, fluffy trifluoroacetate salt. MS MH+=451; $^1$H NMR (CDCl$_3$): δ 9.03 (bs, 1H), 7.85 (s, 2H), 7.75 (s, 1H), 7.04 (s, 1H), 5.86 (s, 1H), 5.52 (s, 2H), 4.64 (s, 2H), 4.3 (2 m, 4H), 2.25 (m, 2H), 2.2 (H2O), 1.46 (s, 18H).

EXAMPLE 2

Compound #55

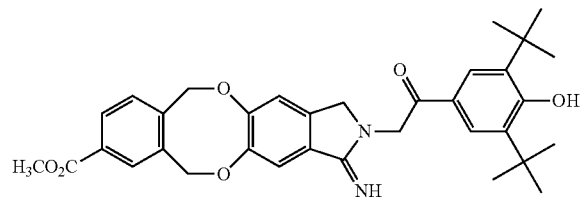 [SMILES: COC(=O)c1ccc2c(c1)COc1cc3c(cc1OC2)CN(CC(=O)c1cc(C(C)(C)C)c(O)c(C(C)(C)C)c1)C3=N]

Step A: Mixture of Regioisomers

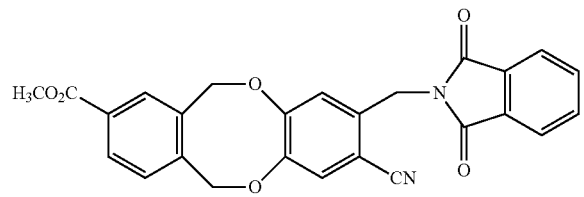

-continued

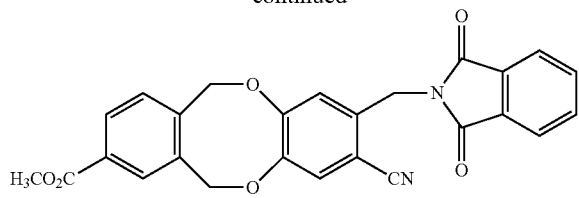

Potassium carbonate (5.52 g, 40 mmol) was added to 2-((1,3-dioxoisoindolin-2-yl)methyl)-4,5-dihydroxybenzonitrile (2.94 g, 10 mmol) in DMF and stirred at room temperature for 10 min. Methyl 3,4-bis(bromomethyl)benzoate (3.40 g, 10.56 mmol, 3B Scientific) was added portionwise as solid over the next 10 min and the resulting mixture was stirred at room temperature for 2 h. The solid was filtered and washed with DMF and the filtrate was evaporated in vacuo to yield an off white solid.

The off-white solid was partitioned between chloroform and water, the organic solution was separated and the aqueous was extracted twice with chloroform. The combined organics were washed twice with brine, dried ($Na_2SO_4$) and evaporated in vacuo to yield a white solid, which was purified by flash column chromatography (DCM:EA 25:1) to yield a mixture of afford a mixture of regioisomers as a white solid. MS MH+ 455; M+Na 477. $^1$H NMR ($CDCl_3$): δ 3.84 (s, 3H), 4.88 (s, 2H), 5.31 (d, J=3.1 Hz, 2H), 5.41 (d, J=12 Hz, 2H), 6.8 (m, 1H), 7.1-7.3 (m, 2H), 7.6-7.9 (m, 6H).

Step B: Mixture of Regioisomers

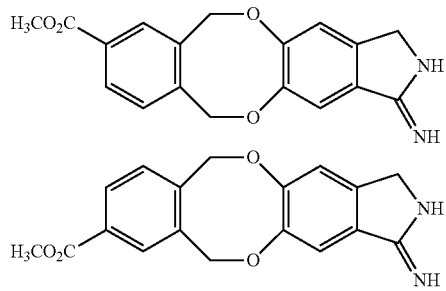

Hydrazine (1.76 g, 55 mmol) was added at room temperature to the regioisomers prepared in STEP A above (2.5 g, 5.5 mmol) in THF (200 mL) and the resulting mixture was stirred at room temperature for 3 h. 1 N HCl (200 mL) was added over the next 5 min and the resulting mixture was stirred at room temperature for 16 h. The resulting mixture was then evaporated in vacuo to yield a white solid, which was triturated twice with water (200 mL) and the aqueous extracts evaporated in vacuo to yield a white solid (impure with hydrazine hydrochloride), which was dried in vacuo for 16 h to yield a residue.

A portion of the residue (6.1 g) was partitioned between ethyl acetate (500 mL) and saturated $NaHCO_3$ (90 mL) with vigorous shaking (5 min). The ethyl acetate was separated and the aqueous extracted again with ethyl acetate (200 mL). The combined organic extract were washed once with brine, dried ($Na_2SO_4$) and evaporated in vacuo to yield a tacky solid (1.71 g). The solid was semi dissolved in methanol (100 mL) and stirred at room temperature for 4 h to effect complete cyclization. The resulting mixture was evaporated in vacuo yield a mixture of the above regioisomers, as a white powder. MS MH+325. $^1$H NMR ($CDCl_3/CD_3OD$) δ 3.92 (s, 3H), 4.42 (s, 1.75 H), 5.4-5.6 (m, 4H), 7.13 (d, J=7.5 Hz, 1H), 7.3-7.5 (m, 2H), 7.9-8.0 (m, 2H).

The regioisomers were co-eluted on reverse phase HPLC (10-90% ACN) and with normal phase thin layer chromatography systems.

Step C: Mixture of Regioisomers

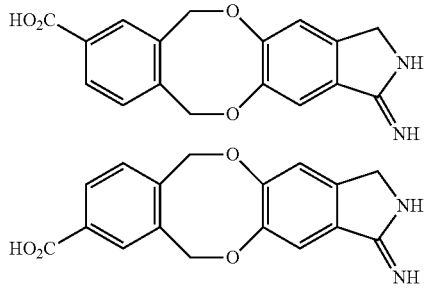

The mixture of regioisomers prepared in STEP B above (400 mg, 1.23 mmol) was combined with lithium hydroxide hydrate (60 mg, 1.42 mmol) in methanol (10 mL) and water (1.0 mL) and refluxed for 3 h. The resulting solution was diluted with methanol (10 mL) and divided into four equal portions, each of which was purified by reverse phase HPLC (10-40% ACN; Kromasil column 10μ C18 100A, 250 mm×50 mm). Fractions containing the second eluting isomer (longer retention time) were combined and evaporated in vacuo to yield a white solid, which was re-dissolved in acetonitrile/water, frozen and lyophilized to yield the 9-carboxy-substituted regioisomer as the corresponding trifluoroacetate salt, as a white fluffy solid. $^1$H NMR ($CD_3OD$) δ 4.64 (s, 2H), 5.53 (s, 2H), 5.63 (s, 2H), 7.29 (s, 1H), 7.43 (d, J=7.8 Hz, 1H), 7.77 (s, 1H), 7.87 (s, 1H), 7.94 (d, J=7.8 Hz, 1H). Fractions containing the 8-carboxy substituted regioisomer were also combined and evaporated in vacuo to yield a white solid.

Step D:

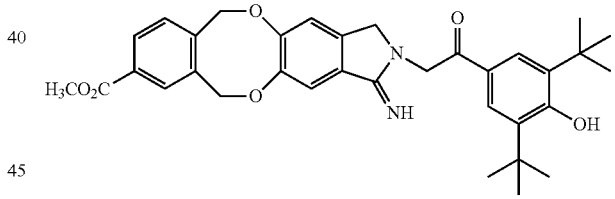

The trifluoroacetate salt of the 9-carboxy-substituted regioisomer prepared in STEP C above (380 mg, 0.90 mmol) was combined with methanol (40 mL) and 4 N HCl in 1,4-dioxane (2.0 mL, 8 mmol) and refluxed for 2 h. Additional 4 N HCl (2 mL) was added and the resulting mixture was maintained at reflux another 3 h until all starting material was consumed, then cooled to room temperature. The resulting solution was evaporated in vacuo to yield the hydrochloride salt of the corresponding methyl ester of the 9-carboxy-substituted compound prepared as in STEP C above. MS MH+ 325.

The hydrochloride salt (350 mg, 0.80 mmol) and diisopropylethylamine (600 mg, 4.65 mmol) were combined in DMF (25 mL) and stirred 20 min. 90% 4-hydroxy-3,5-di(t-butyl) bromoacetophenone (390 mg, 1.07 mmol, ABCR Corp.) was added over the next 2 min and resulting mixture was stirred at room temperature for 16 h. The resulting solution was diluted with ethyl acetate (150 mL) and water (100 mL) and shaken vigorously for 5 min. The resulting solid was filtered and washed with ethyl acetate, then air dried to yield the title compound as an off-white solid, which was combined with an equivalent of 48% HBr (76 mg, 0.45 mmol) and evaporated in vacuo to yield the title compound as its corresponding HBr salt, as a light yellow solid. HPLC single peak—98%; MS MH+ 571. ¹H NMR (CD₃OD) δ 1.46 (s, 18H), 3.89 (s, 3H), 4.73 (s, 2H), 5.39 (s, 2H), 5.55 (s, 2H), 5.65 (s, 2H), 7.29 (s, 1H), 7.45 (d, J=7.8 Hz, 1H), 7.78 (s, 1H), 7.88 (s, 2H), 7.9-8.0 (m, 2H).

EXAMPLE 3

Compound #72

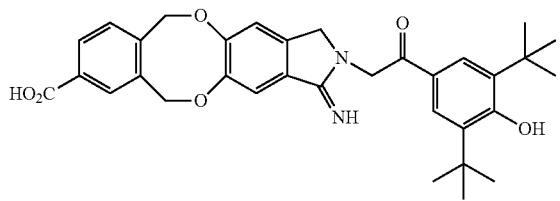 [SMILES: CC(C)(C)c1cc(C(=O)CN2Cc3cc4c(cc3C2=N)OCc2cc(C(=O)O)ccc2CO4)cc(C(C)(C)C)c1O]

The mixture of esters prepared as in Example 2, STEP B above (195 mg, 0.60 mm) in DMF (15 mL) was combined with DIPEA (387 mg, 3.0 mm) and 90% 4-hydroxy-3,5-di(t-butyl)bromoacetophenone (262 mg, 0.72 mmol, ABCR Corp.) and the resulting mixture stirred at room temperature for 6 h. The resulting mixture was evaporated in vacuo to yield an oil, which was purified via reverse phase HPLC to yield a solid, which was partitioned between CHCl₃ and saturated NaHCO₃. The CHCl₃ was washed once with brine, dried (Na₂SO₄) and evaporated in vacuo to a yellow solid residue (187 mg, 55%). A portion (100 mg) of the yellow solid residue was combined with LiOH (18.5 mg, 0.44 mm) in methanol (8 mL) and water (0.80 mL) and refluxed for 4 h. The resulting solution was evaporated in vacuo to yield a solid, which was purified via reverse phase HPLC to yield the title compound as its corresponding trifluoroacetate salt. MS MH+=557; ¹H NMR (CDCl₃/CD₃OD) δ 1.47 (s, 18H), 4.65 (s, 2H), 5.42 (s, 2H), 5.50 (s, 2H), 5.61 (s, 2H), 7.11 (s, 1H), 7.3-7.4 (m, 1H), 7.85 (s, 2H), 7.91 (s, 1H), 7.88-8.0 (m, 2H).

EXAMPLE 4

(Z)-1-(3,5-di-tert-butyl-4-hydroxyphenyl)-2-(8-imino-2H-[1,4]-dioxocino[2,3-f]isoindol-9(5H,8H,10H)-yl)ethanone Compound #100

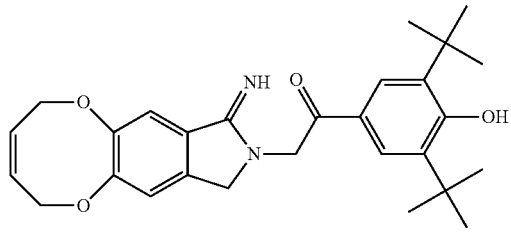 [SMILES: CC(C)(C)c1cc(C(=O)CN2Cc3cc4c(cc3C2=N)OC/C=C\CO4)cc(C(C)(C)C)c1O]

Step A:

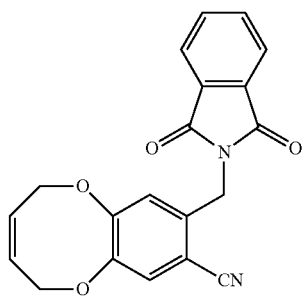 [SMILES: N#Cc1cc2c(cc1CN1C(=O)c3ccccc3C1=O)OC/C=C\CO2]

cis-1,4-Dichloro-2-butene (0.200 g, 1.6 mmol), 2((1,3-dioxoisoindolin-2-yl)methyl)-4,5-dihydroxybenzonitrile (0.500 g, 1.7 mmol), and potassium carbonate (0.77 g, 5.6 mmol) were suspended in dry DMF (80 ml) and heated to 50° C. for 5 h. The resulting mixture was cooled to room temperature and stirred overnight, then filtered. The filtrate was diluted with ethyl acetate, washed with water (2×), brine (2×), dried (Na₂SO₄) and concentrated in vacuo. The resulting residue was chromatographed eluting with ethyl acetate/heptanes (50:50) to yield (Z)-9-((1,3-dioxoisoindolin-2-yl)methyl)-2,5-dihydrobenzo[b][1,4]dioxocine-8-carbonitrile as a residue. ¹H NMR (CDCl₃): δ 7.94-7.86 (m, 2H), 7.78-7.73 (m, 2H), 7.32 (s, 1H), 6.83 (s, 1H), 5.92-5.85 (m, 2H), 4.98 (s, 4H), 4.80 (s, 2H).

Step B:

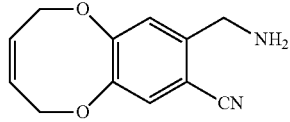 [SMILES: N#Cc1cc2c(cc1CN)OC/C=C\CO2]

The residue prepared in STEP A above (0.34 g, 0.98 mmol) and hydrazine (0.31 ml, 9.8 mmol) were dissolved in THF (34 ml) and stirred at room temperature for 5 h. 1N HCl (22 mL) was added and the resulting mixture stirred overnight. The resulting mixture was then concentrated in vacuo and the residue was triturated with water. The water triturations were combined and concentrated in vacuo. The resulting solid was partition between ethyl acetate (50 ml) and saturated sodium bicarbonate (10 mL). The aqueous layer was extracted with ethyl acetate. The organic layers were combined, washed with brine (20 ml), dried (Na₂SO₄) and concentrated in vacuo to yield (Z)-9-(aminomethyl)-2,5-dihydrobenzo[b][1,4]dioxocine-8-carbonitrile as a residue.

Step C:

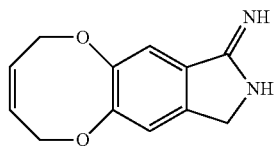 [SMILES: N=C1NCc2cc3c(cc21)OC/C=C\CO3]

The residue prepared in STEP B above (0.174 g, 0.80 mmol) was dissolved in dry methanol (30 ml) and heated to 40° C. for 2 h. The resulting mixture was concentrated in vacuo to yield (Z)-9,10-dihydro-2H-[1,4]dioxocino[2,3-f]isoindol-8(5H)-imine as a residue. ¹H NMR (CD₃OD): δ 7.39 (s, 1H), 7.07 (s, 1H), 5.93-5.90 (m, 2H), 5.01 (d, 2H), 4.42 (s, 2H), 3.34 m, 2H).

Step D

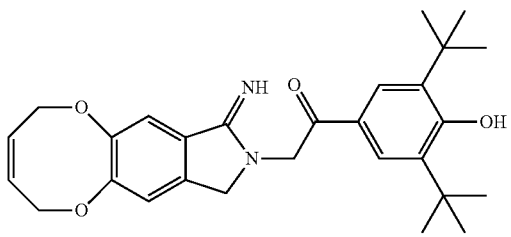 [SMILES: CC(C)(C)c1cc(C(=O)CN2Cc3cc4c(cc3C2=N)OC/C=C\CO4)cc(C(C)(C)C)c1O]

The residue prepared as in STEP C above (0.038 g, 0.17 mmol), 2-bromo-1-[3-5-di(t-butyl)-4-hydroxyphenyl)ethan-1-one (0.059 g, 0.18 mmol) and diisopropylethylamine (0.059 ml, 0.34 mmol) were dissolved in DMF (3 ml) and the resulting mixture stirred at room temperature for 2 h. The resulting mixture was then diluted with dichloromethane, washed with water (3×5 ml), saturated sodium bicarbonate (5 ml), dried ($Na_2SO_4$) and concentrated in vacuo. The resulting residue was chromatographed eluting with dichloromethane/methanol/ammonium hydroxide (97:3:0.5) to yield the title compound as a residue. $^1$H NMR (DMSO): δ7.90 (s, 1H), 7.42 (s, 2H), 7.30 (s, 1H), 5.99-5.94 (m, 2H), 5.15 (s, 2H), 5.07-5.00 (m, 2H), 4.90 (bs, 2H), 4.68 (s, 2H), 1.32 (s, 18). Ms MH+=463.

EXAMPLE 5

Compound #103

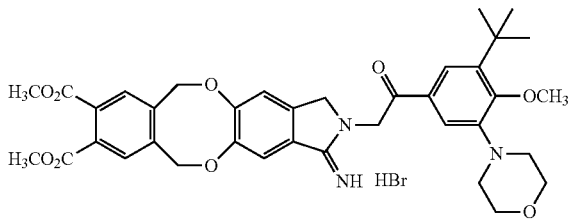 [SMILES: COC(=O)c1cc2c(cc1C(=O)OC)COc1cc3c(cc1OC2)CN(CC(=O)c1cc(N2CCOCC2)c(OC)c(C(C)(C)C)c1)C3=N ; Br]

Step A:

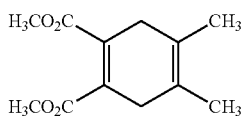

2,3-Dimethyl-buta-1,3-diene (2.0 g, 24.3 mmol) and but-2-ynedioic acid dimethyl ester in benzene (14 mL) were heated to reflux for 16 h. The resulting mixture was cooled and evaporated in vacuo to yield a solid, which was purified via flash column chromatography (EtOAc/heptane 9:1) to yield 4,5-dimethyl-cyclohexa-1,4-diene-1,2-dicarboxylic acid dimethyl ester as a white solid.

Step B:

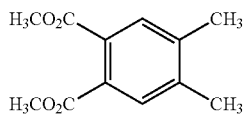

To a solution of 4,5-dimethyl-cyclohexa-1,4-diene-1,2-dicarboxylic acid dimethyl ester (3.84 g, 17.1 mmol) in chlorobenzene was added 2,3-dichloro-5,6-dicyano-1,4-benzoquinone (DDQ) (7.77 g, 34.2 mmol) at room temperature and the resulting mixture was heated to reflux 48 h. The resulting mixture was cooled and filtered through FLORISIL®. The pad of FLORISIL® was rinsed with diethyl ether and the filtrate filtered another (3×) through a pad of FLORISIL®. The filtrate was evaporated in vacuo to yield an amber syrup, which was purified via flash column chromatography (EtOAc/Heptane 4:1) to yield 4,5-dimethyl-phthalic acid dimethyl ester as a colorless oil.

Step C:

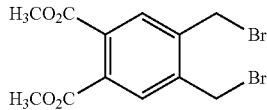

A solution of 4,5-dimethyl-phthalic acid dimethyl ester (1.01 g, 4.54 mmol), N-bromosuccinimide (NBS, 1.70 g, 9.5 mmol) and benzoyl peroxide (49 mg, 0.2 mmol) in carbon tetrachloride (10 mL) was heated to 60° C. for 24 h. The resulting slurry was cooled to room temperature then filtered through a pad of CELITE and evaporated in vacuo to yield a syrup, which was purified via flash column chromatography (EtOAc/heptane 4:1) to yield 4,5-bis-bromomethyl-phthalic acid dimethyl ester was a white solid.

Step D:

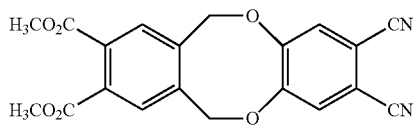 [SMILES: COC(=O)c1cc2c(cc1C(=O)OC)COc1cc(C#N)c(C#N)cc1OC2]

A slurry of 4,5-bis-bromomethyl-phthalic acid dimethyl ester (1.57 g, 4.12 mmol), 4,5-dihydroxy-phthalonitrile (660 mg, 4.12 mmol) and potassium carbonate (1.1 g, 8.24 mmol) in DMF (20 mL) was heated to 60° C. for 1 h under an atmosphere of argon. The resulting slurry was cooled to room temperature and diluted with water. A white precipitate was collected via filtration and re-crystallized from EtOAc to yield 2,3-dicyano-6,11-dihydro-5,12-dioxa-dibenzo[a,e]cyclooctene-8,9-dicarboxylic acid dimethyl ester as a white solid. $C_{20}H_{14}N_2O_6$; MS (ESI) m/z 378.9 (MH)$^+$.

Step E:

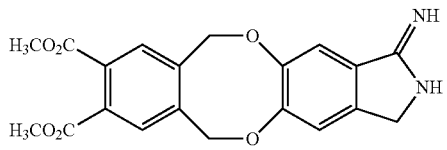 [SMILES: COC(=O)c1cc2c(cc1C(=O)OC)COc1cc3c(cc1OC2)CNC3=N]

A slurry of 2,3-dicyano-6,11-dihydro-5,12-dioxa-dibenzo[a,e]cyclooctene-8,9-dicarboxylic acid dimethyl ester (280 mg) and RANEY® Ni (28 mg) in EtOH/toluene (3:1, 16 mL) was shaken in a Parr apparatus under 60 psi hydrogen at room temperature for 16 h. The resulting mixture was filtered through CELITE and evaporated in vacuo to yield a tan solid. C$_{20}$H$_{18}$N$_2$O$_6$; MS (ESI) m/z 383.0 (MH)$^+$.
Step F:

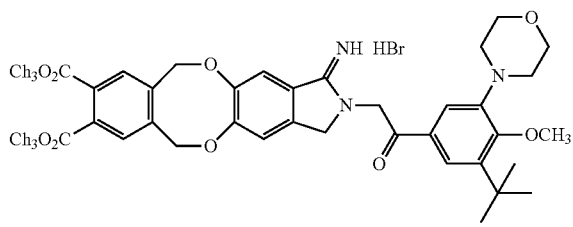

A solution of the tan solid prepared in STEP E above (72 mg, 0.19 mmol) and 2-bromo-1-(3-tert-butyl-4-methoxy-5-morpholin-4-yl-phenyl)-ethanone (70 mg, 0.19 mmol) in THF (3 mL) stirred for 1 hr at room temperature then evaporated in vacuo to yield a solid which was purified via reverse-phase column chromatography eluted with acetonitrile/water to yield title compound as its corresponding HBr salt, as a white solid. $^1$H NMR (CD$_3$OD) δ 7.72 (s, 1H), 7.64 (s, 1H), 7.63 (s, 1H), 7.53 (s, 1H), 7.48 (d, J=1.9 Hz, 1H), 7.21 (s, 1H), 5.57 (s, 2H), 5.46 (s, 2H), 5.31 (s, 2H), 4.65 (s, 2H), 3.93 (s, 3H), 3.81-3.77 (ov m, 10H), 2.98 (m, 4H), 1.32 (s, 9H). C$_{37}$H$_{41}$N$_3$O$_9$; MS (ESI) m/z 671.8 (MH)$^+$.

EXAMPLE 6

Compound #82 and #83

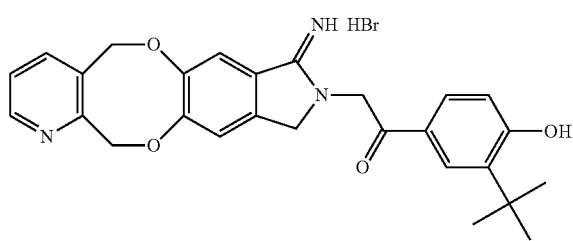

and

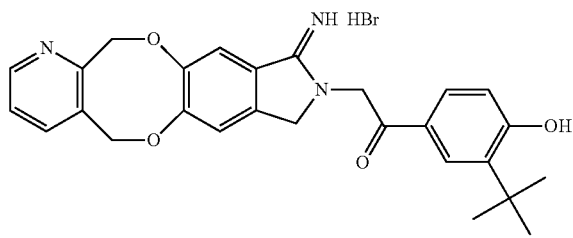

Step A:

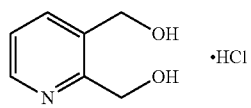

To a solution of pyridine-2,3-dicarboxylic acid dimethyl ester (25.0 g, 128.1 mmol) in ethanol (183 mL) was added sodium borohydride (24.2 g, 640.5 mmol). The resulting mixture was cooled to 5° C. while stirring under argon. A solution of calcium chloride (12.6 g, 113.5 mmol) in ethanol (77 mL) was added dropwise while maintaining a temperature between 10° C. and 15° C. After addition, the resulting mixture was allowed to warm to room temperature over 16 h. A mixture of 4:1 water/ethanol (100 mL) added and the resulting mixture stirred 1 hr, then evaporated in vacuo to yield a white solid, which was finely ground with mortar and pestle. The fine powder was refluxed for 3 h in ethanol (450 mL), cooled to room temperature and filtered through dicalite. The filtrate was filtered through Nylon 66, 0.45-μ filter, then treated with anhydrous hydrogen chloride gas until solution was pH 2 while cooling on ice bath. A white precipitate was isolated and washed with ethyl ether and dried to yield (2-hydroxymethyl-pyridin-3-yl)-methanol hydrogen chloride as a white solid. C$_7$H$_9$NO$_2$; MS (ESI) m/z 140.1 (MH)$^+$.
Step B:

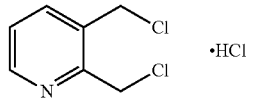

(2-Hydroxymethyl-pyridin-3-yl)-methanol hydrogen chloride (26.79 g, 122 mmol) was added to thionyl chloride (33.8 mL) at 5° C. under an atmosphere of argon. The resulting mixture was allowed to warm to room temperature with stirred over 16 h. The resulting mixture was then evaporated in vacuo to yield 2,3-bis-chloromethyl-pyridine hydrogen chloride as a white solid.
Step C:

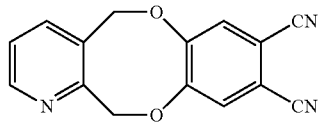 [SMILES: N#Cc1cc2c(cc1C#N)OCc1ncccc1CO2]

A slurry of 2,3-bis-chloromethyl-pyridine hydrogen chloride (6.63 g, 31.2 mmol), 4,5-dihydroxy-phthalonitrile (5.0 g, 31.2 mmol) and potassium carbonate (15.1 g, 109.2 mmol) in DMF (150 mL) was heated to 80° C. for 1.5 h under an atmosphere of argon. The resulting slurry was cooled to room temperature and quenched with ice. A white precipitate was collected via filtration to yield 5,12-dihydro-6,1'-dioxa-1-aza-dibenzo[a,e]cyclooctene-8,9-dicarbonitrile as a white solid. C$_{15}$H$_9$N$_3$O$_2$; MS (ESI) m/z 263.0 (MH)$^+$.
Step D: Mixture of

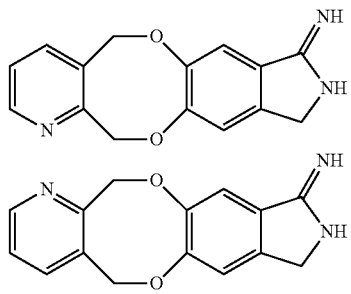

A slurry of 5,12-dihydro-6,1-dioxa-1-aza-dibenzo[a,e]cyclooctene-8,9-dicarbonitrile (2.66 g, 10.1 mmol), Raney® Ni (2.84 g) and sodium acetate (1.3 g, 15.8 mmol) in EtOH/toluene (3:1, 1 L) was shaken in a Parr apparatus under 60 psi hydrogen at room temperature for 16 h. The resulting mixture was filtered through CELITE and evaporated in vacuo to yield a solid which was then purified via silica gel column eluted with (7:3) EtOAc/heptanes to yield a 1:1 mixture of isomers. $C_{15}H_{13}N_3O_2$: MS (ESI) m/z 268.0 (MH)$^+$.

Step E:

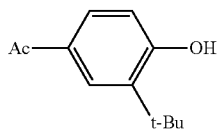 [SMILES: CC(=O)c1ccc(O)c(C(C)(C)C)c1]

To a solution of aluminum chloride (162.3 g, 1.22 mol) in methylene chloride (600 mL) at −75° C. was added acetyl chloride (95.7 g, 1.22 mol) while stirring under an atmosphere of argon. 2-tert-Butyl-phenol (167 g, 1.11 mol) was added dropwise over 1 hr. The resulting mixture was allowed to warm to 0° C. for 10 min. The resulting mixture was then quenched with ice and extracted with EtOAc (1.5 L). The organic layer was separated and dried with brine. The organic layer was evaporated in vacuo to yield a white solid. The white solid was dissolved in methanol (300 mL) and treated with potassium carbonate (100 g) and the resulting mixture allowed to stir 18 h at room temperature. Water (300 mL) was added and pH adjusted to 5 to 6 using concentrated hydrochloric acid. The resulting mixture was extracted with EtOAc. The organic layer was rinsed with brine and dried over sodium sulfate, then evaporated in vacuo to yield 1-(4-tert-butyl-3-hydroxy-phenyl)-ethanone as a tan solid. $C_{12}H_{16}O_2$; MS (ESI) m/z 193.2 (MH)$^+$.

Step F:

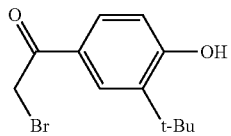 [SMILES: CC(C)(C)c1cc(C(=O)CBr)ccc1O]

A solution of 1-(4-tert-Butyl-3-hydroxy-phenyl)-ethanone (192 mg, 1.0 mmol) and trimethyl-phenyl-ammonium tribromide in (3:1) tetrahydrofuran/methanol (3 mL) was stirred at room temperature 1 h. The resulting mixture was quenched with 5% wt. aq. sodium thiosulfate (500 μL) then water (3.5 mL). DCM added and the organic layer separated, dried over sodium sulfate, filtered and evaporated in vacuo to yield an amber syrup. The syrup was purified via silica gel chromatography eluting with (3:1) EtOAc/heptanes to yield 2-bromo-1-(3-tert-butyl-4-hydroxy-phenyl)-ethanone as a white solid. $C_{12}H_{15}BrO_2$; MS (ESI) m/z 271/273 (MH)$^+$.

Step G: Mixture of

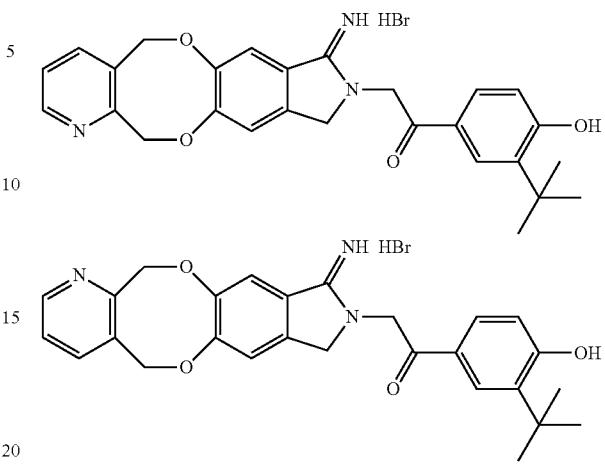

A slurry of the compound prepared as in STEP D (67 mg, 0.25 mmol) and 4-bromomethyl-2-tert-butyl-phenol (67 mg, 0.25 mmol) in (1:1) THF:DMF (10 mL) was stirred for 1 h at room temperature then evaporated in vacuo to yield a solid which was purified via reverse-phase column chromatography eluted with acetonitrile/water to yield the mixture of title compounds, as a two separated isomers. $^1$H NMR (CD$_3$OD) δ 8.49 (d, J=4.6 Hz, 1H), 7.95 (s, 1H), 7.81-7.77 (ov m, 3H), 7.43-7.38 (ov m, 2H), 6.87 (d, J=8.3 Hz, 1H), 5.62 (s, 2H), 5.55 (s, 2H), 5.36 (s, 2H), 4.75 (s, 2H), 1.42 (s, 9H). $C_{27}H_{27}N_3O_4$; MS (ESI) m/z 458.0 (MH)$^+$; $^1$H NMR (CD$_3$OD) δ 8.42 (dd, J=5.1 Hz, J=1.3 Hz, 1H), 7.87-7.81 (ov m, 3H), 7.69 (dd, J=8.6 Hz, J=1.8 Hz, 1H), 7.38 (dd, J=7.6 Hz, J=5.0 Hz, 1H), 7.16 (s, 1H), 6.78 (d, J=8.4 Hz, 1H), 5.61 (s, 2H), 5.47 (s, 2H), 5.26 (s, 2H), 4.64 (s, 2H), 1.32 (s, 9H). $C_{27}H_{27}N_3O_4$; MS (ESI) m/z 458.0 (MH)$^+$.

EXAMPLE 7

1-(3,5-di-tert-butyl-4-hydroxyphenyl)-2-(3-(2-(dimethylamino)ethyl)-7-imino-3,4-dihydro-[1,4]dioxepino[2,3-f]isoindol-8(2H,7H,9H)-yl)ethanone Compound #16

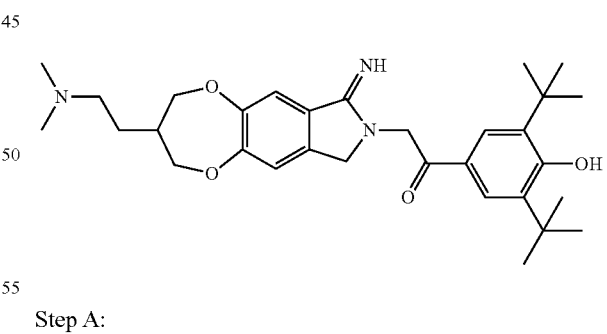

Step A:

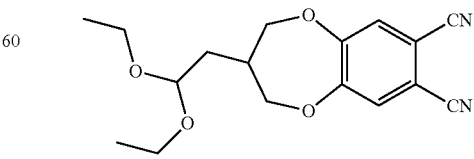

To the mixture of 4,5-dihydroxy-phthalonitrile (2.50 g, 15.6 mmol), 2-(2,2-diethoxy-ethyl)-propane-1,3-diol (4.5 g, 23.4 mmol) and triphenylphosphine (6.138 g, 23.4 mmol) in THF (40 mL) was added diethyl azodicarboxylate (4.08 g, 23.4 mmol) and the resulting mixture heated at 75° C. overnight. The resulting mixture was then cooled to room temperature and evaporated in vacuo to yield a solid, which was purified via flash column chromatography (EA/Hex 2:3) to yield 3-(2,2-diethoxyethyl)-3,4-dihydro-2H-benzo[b][1,4]dioxepine-7,8-dicarbonitrile as a white solid. MS MH+=317, $^1$H NMR (CDCl$_3$) δ 7.29 (s, 2H), 4.58 (m, 1H), 4.46 (m, 2H), 4.19 (m, 2H), 3.66 (m, 2H), 3.52 (m, 2H), 2.60 (m, 1H), 1.78 (m, 2H), 1.20 (t, J=7.0 Hz, 6H).

Step B:

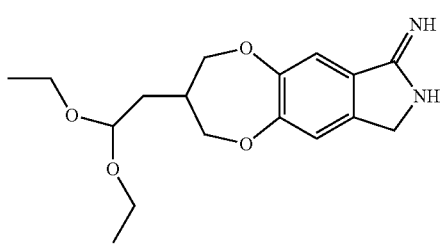 [SMILES: CCOC(CC1COc2cc3c(cc2OC1)C(=N)NC3)OCC]

The solid prepared n STEP A above (800 mg, 2.5 mmol) was semi-dissolved in absolute methanol (50 mL) and combined with PtO$_2$ (100 mg) and shaken on a Parr shaker under 35 psi of hydrogen at room temperature for 24 h. The resulting solution was filtered through dicalite and the filtrate was evaporated in vacuo to yield a light green solid, which was dissolved in CHCl$_3$/MeOH (40:1), dried (Na$_2$SO$_4$) and evaporated in vacuo to yield 3-(2,2-diethoxyethyl)-3,4,8,9-tetrahydro-[1,4]dioxepino[2,3-f]isoindol-7(2H)-imine which was used in the next step without further purification. MS MH+=321.

Step C:

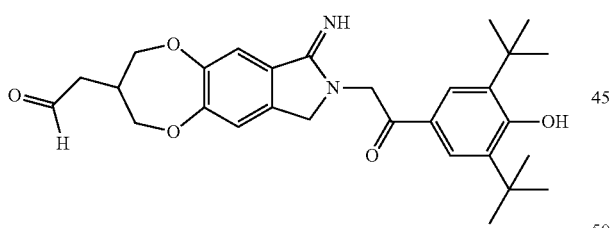

(Compound #14)

The residue prepared in STEP B above (850 mg, 2.65 mmol) in DMF (10 mL) was combined with 2-bromo-1-[3,5-di(tert-butyl)-4-hydroxyphenyl]ethan-1-one (1.04 g, 3.18 mmol) and stirred at room temperature for 18 h. The resulting mixture was evaporated in vacuo to yield an oil, which was treated with 50% TFA in DCM at 0° C. The solvent was then evaporated, and the residue purified via reverse phase HPLC to yield 2-(8-(2-(3,5-di-tert-butyl-4-hydroxyphenyl)-2-oxoethyl)-7-imino-2,3,4,7,8,9-hexahydro-[1,4]dioxepino[2,3-f]isoindol-3-yl)acetaldehyde as its corresponding trifluoroacetate salt, as a residue. MS MH+=493; $^1$H NMR (CDCl$_3$): d 8.88 (bs, 1H), 7.83 (s, 2H), 7.66 (s, 1H), 7.05 (s, 1H), 5.85 (bs, 1H), 4.67 (s, 2H), 4.36 (m, 2H), 4.11 (m, 4H), 2.91 (m, 1H), 2.76 (m, 2H), 1.45 (s, 18H).

Step D:

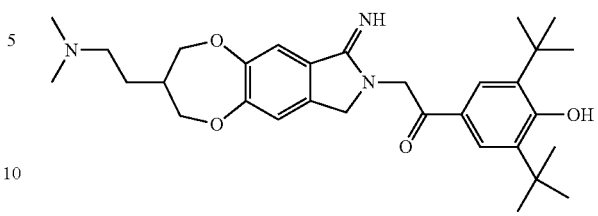

To a mixture of the residue prepared in STEP C above (31 mg, 0.043 mmol) and 2M dimethylamine in THF (22 μl, 0.043 mmol) in 1,2-dichloroethane (5 mL) was added two drops of HOAc. The resulting mixture was stirred at room temperature for 3 h. Then NaBH(OAc)$_3$ (9 mg, 0.043 mmol) was added and the resulting mixture stirred at room temperature for 1 h. The resulting mixture was then quenched with saturated NaHCO$_3$, extracted with EtOAc, washed with water and then brine; dried with and concentrated to yield a residue which was purified via reverse phase HPLC to yield the title compound as its corresponding trifluoroacetate salt, as a residue. MS MH+=522; $^1$H NMR (CD$_3$OD): δ 7.91 (s, 2H), 7.69 (s, 1H), 7.27 (s, 1H), 5.42 (s, 2H), 4.77 (s, 2H), 4.42 (m, 2H), 4.24 (m, 2H), 2.93 (s, 6H), 2.40 (m, 1H), 1.95 (m. 2H), 1.47 (s, 20H).

EXAMPLE 8

Compound #74

Step A:

To a mixture of 4,5-dihydroxy-phthalonitrile (1 g, 6.24 mmol) in DMF (30 mL), was added 3,4-bis-chloromethyl-2,5-dimethyl-thiophene (1.31 g, 6.24 mmol), followed by addition of CsCO$_3$ (5.08 g, 15.6 mmol). The resulting mixture was then heated to 80° C., overnight. The resulting mixture was then cooled to room temperature and evaporated in vacuo to yield a solid, which was purified via flash column chromatography (EA/Hex 2:3) to yield a white solid. MS MH+=297; $^1$H NMR (CDCl$_3$) δ 7.26 (s, 2H), 5.29 (s, 4H), 2.35 (s, 6H).

Step B:

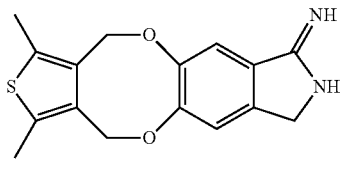 [SMILES: Cc1sc(C)c2c1COc1cc3c(cc1OC2)C(=N)NC3]

The solid prepared in STEP A above (0.6 g, 2.02 mmol) was semi-dissolved in absolute MeOH (200 mL) with PtO$_2$ (700 mg) and shaken on a Parr shaker under hydrogen at room temperature for 24 h. The resulting solution was filtered through dicalite and the filtrate was evaporated in vacuo to yield a solid, which was used in the next step without further purification. MS MH+=301.

Step C:

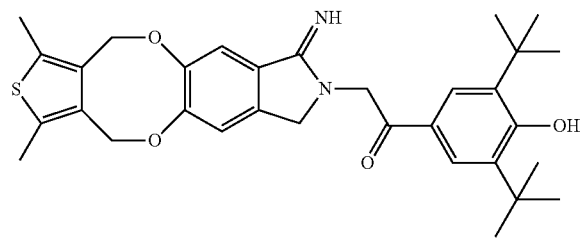 [SMILES: Cc1sc(C)c2c1COc1cc3c(cc1OC2)C(=N)N(CC(=O)c1cc(C(C)(C)C)c(O)c(C(C)(C)C)c1)C3]

The solid prepared in STEP B above (0.104 g, 0.347 mmol) in DMF (6 mL) was combined with 2-bromo-1-[3,5-di(tert-butyl)-4-hydroxyphenyl]ethan-1-one (0.17 g, 0.52 mmol) and stirred at room temperature for 18 h. The resulting mixture was then evaporated in vacuo to yield an oil, which was purified via reverse phase HPLC to yield the title compound as its corresponding TFA salt. MS MH+=547; $^1$H NMR (CD$_3$OD) δ 7.89 (s, 2H), 7.75 (s, 1H), 7.21 (s, 1H), 5.46 (s, 2H), 5.39 (s, 2H), 5.32 (s, 2H), 4.72 (s, 2H), 2.35 (s, 3H), 2.26 (s, 3H), 1.46 (s, 18H).

EXAMPLE 9

1-(3-tert-butyl-4-methoxy-5-morpholinophenyl)-2-(3,3,4,4-tetrafluoro-8-imino-4,5-dihydro-2H-[1,4]-dioxocino[2,3-f]isoindol-9(3H,8H,10H)-yl)ethanone
Compound #90

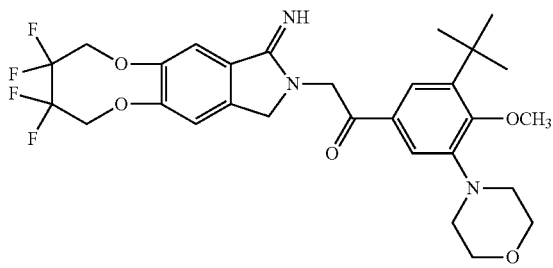 [SMILES: COc1c(N2CCOCC2)cc(C(=O)CN2Cc3cc4c(cc3C2=N)OCC(F)(F)C(F)(F)CO4)cc1C(C)(C)C]

Step A:

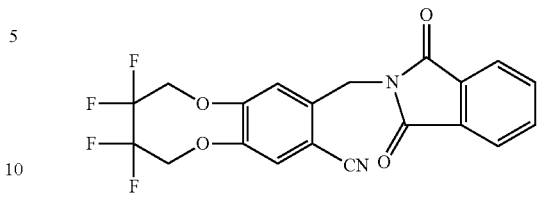

2,2,3,3-Tetrafluorobutane-1,4-diol (0.207 g, 1.28 mmol) in DCM was cooled to 0° C. Pyridine (0.25 g, 3.19 mmol) was added, followed by addition of triflate anhydride (0.78 g, 2.75 mmol). The resulting mixture was then stirred at room temperature for an additional 1 h, and then diluted with DCM. The resulting mixture was washed with water, brine, then dried (Na$_2$SO$_4$) and concentrated to yield trifluoromethanesulfonic acid 2,2,3,3-tetrafluoro-4-trifluoromethanesulfonyloxy-butyl ester as white solid (0.45 g). The white solid (0.356 g, 0.835 mmol) in DMF (5 mL) was added dropwise to a mixture of 2-(1,3-dioxo-1,3-dihydro-isoindol-2-ylmethyl)-4,5-dihydroxy-benzonitrile (0.18 g, 0.62 mmol) and K$_2$CO$_3$ (0.17 g, 1.23 mmol) in DMF (5 mL) at 75° C. After addition, the resulting mixture was maintained at 75° C. for an additional 1 h. The resulting solid was filtered out and the filtrate evaporated to yield a residue. (0.2 g). MS MH+=421.

Step B:

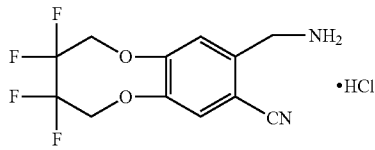 [SMILES: N#Cc1cc2c(cc1CN)OCC(F)(F)C(F)(F)CO2 ; Cl]

To the residue prepared in STEP A above (0.2 g, 0.48 mmol) in THF (10 mL) was added anhydrous hydrazine (0.15 mL, 4.8 mmol). The resulting mixture was stirred at room temperature for 2 h, then treated with 1 N HCl to yield a residue, which was used in the next step without further purification. MS MH+=291.

Step C:

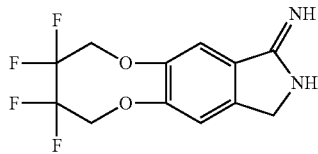 [SMILES: N=C1NCc2cc3c(cc21)OCC(F)(F)C(F)(F)CO3]

To the residue prepared in STEP B above (0.25 g, 0.61 mmol) in dry MeOH (10 mL) and DMF (5 mL) was added K$_2$CO$_3$ (0.2 g, 1.44 mmol). The resulting mixture was stirred at 40° C. for 3 h. The solid was filtered out and the filtrate was evaporated. The resulting residue was re-dissolved in EtOAc, washed with water and brine. The organic layers were combined and dried with Na$_2$SO$_4$, and then concentrated to yield a residue. The residue was used in the next step with further purification. MS MH+=291.

Step D:

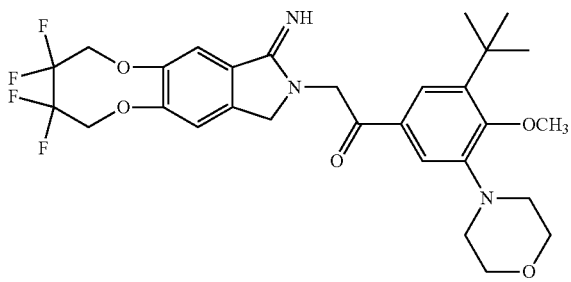 [SMILES: COc1c(N2CCOCC2)cc(C(=O)CN2Cc3cc4c(cc3C2=N)OCC(F)(F)C(F)(F)CO4)cc1C(C)(C)C]

The residue prepared in STEP C above (71.7 mg, 0.247 mmol) in DMF (5 mL) was combined with 2-bromo-1-[3-tert-butyl-4-methoxy-5-morpholin-4-yl-phenyl]ethanone (91.5 mg, 0.247 mmol), DIEA (0.1 mL) and stirred at room temperature for 18 h. The resulting mixture was then evaporated in vacuo to yield an oil, which was purified via reverse phase HPLC to yield the title compound as a residue. MS MH+=580; $^1$H NMR (CD$_3$OD) δ 7.88 (s, 1H), 7.75 (s, 1H), 7.59 (s, 1H), 7.47 (s, 1H), 5.46 (s, 2H), 4.74 (m, 6H), 4.03 (s, 3H), 3.90 (t, J=4.5 Hz, 4H), 3.08 (t. J=4.4 Hz, 4H), 1.43 (s, 9H).

EXAMPLE 10

1-(3-tert-butyl-4-methoxy-5-morpholinophenyl)-2-(9-imino-3,4,5,6-tetrahydro-[1,4,7]dioxazonino[2,3-f]isoindol-10(2H,9H,11H)-yl)ethanone Compound #42

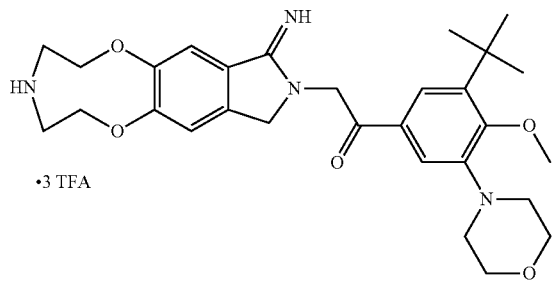 [SMILES: COc1c(N2CCOCC2)cc(C(=O)CN2Cc3cc4c(cc3C2=N)OCCNCCO4)cc1C(C)(C)C]

Step A:

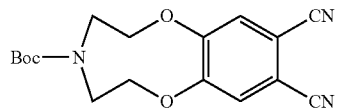 [SMILES: CC(C)(C)OC(=O)N1CCOc2cc(C#N)c(C#N)cc2OCC1]

To the mixture of 4,5-dihydroxy-phthalonitrile (1.28 g, 8 mmol), bis-(2-hydroxy-ethyl)-carbamic acid tert-butyl ester (1.97 g, 9.6 mmol), triphenyl phosphine (6.30 g, 24 mmol) in THF (200 mL) was added DEAD (4.17 g, 24 mmol) and the resulting mixture was heated at 80° C. overnight. The resulting mixture was then cooled to room temperature and diluted with EtOAc, washed with 10% Na$_2$CO$_3$, brine, then evaporated in vacuo to yield a solid, which was purified via flash column chromatography (EA/Hex 2:3) to yield a white solid. MS MH+=330, $^1$H NMR (CDCl$_3$) δ 7.20 (s, 2H), 4.20 (m, 4H), 3.36 (m, 4H), 1.40 (s, 9H).

Step B:

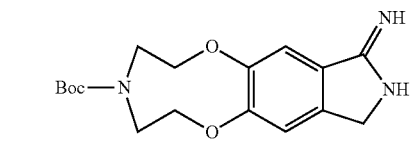 [SMILES: CC(C)(C)OC(=O)N1CCOc2cc3c(cc2OCC1)C(=N)NC3]

The solid prepared in STEP A above (0.36 g, 1.1 mmol) was semi-dissolved in absolute MeOH (20 mL) with PtO$_2$ (50 mg) and shaken on a Parr shaker under hydrogen at room temperature for 24 h. The resulting solution was filtered through dicalite and the filtrate was evaporated in vacuo to yield a solid, which was used in the next step without further purification. MS MH+=334.

Step C:

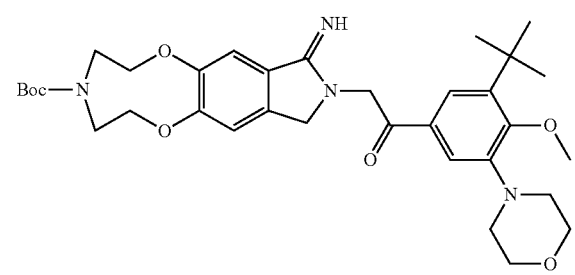 [SMILES: COc1c(N2CCOCC2)cc(C(=O)CN2Cc3cc4c(cc3C2=N)OCCN(C(=O)OC(C)(C)C)CCO4)cc1C(C)(C)C]

The solid prepared in STEP B above (62.5 mg, 0.19 mmol) in DMF (5 mL) was combined with 2-bromo-1-(3-tert-butyl-4-methoxy-5-morpholin-4-yl-phenyl)-ethanone (69.4 mg, 0.19 mmol), DIEA (32.6 uL, 0.19 mmol) and stirred at room temperature for 18 h. The resulting mixture was evaporated in vacuo to yield an oil, which was purified via reverse phase HPLC to yield tert-butyl 10-(2-(3-tert-butyl-4-methoxy-5-morpholinophenyl)-2-oxoethyl)-9-imino-2,3,5,6,10,11-hexahydro-[1,4,7]dioxazonino[2,3-f]isoindole-4(9H)-carboxylate (Compound #41), as its corresponding TFA salt, as a residue. MS MH+=623; $^1$H NMR (CD$_3$OD) δ 7.77 (s, 1H), 7.65 (s, 1H), 7.59 (s, 1H), 7.24 (d, J=16 Hz, 1H), 4.60 (m, 2H), 4.46 (m, 2H), 4.02 (m, 2H), 3.90 (m, 6H), 3.60 (m, 5), 3.08 (m, 4H), 1.93 (m, 2H), 1.42 (s, 9H), 1.25 (s, 9H).

Step D:

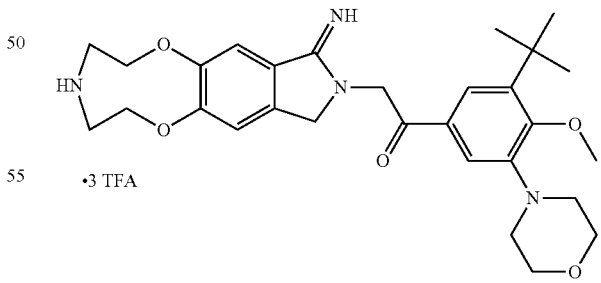

To a mixture of the residue prepared in STEP C above 41 mg, 0.066 mmol) in DCM (5 mL) was added TFA (2 mL). The resulting mixture stirred at room temperature for 1 h. The solvent was evaporated in vacuo to yield an oil, which was purified via reverse phase HPLC to yield the title compound, as its corresponding TFA salt, as a residue. MS MH+=523; $^1$H NMR (CD$_3$OD): δ 7.91 (s, 1H), 7.75 (s, 1H), 7.59 (s, 1H), 7.50 (s, 1H), 5.49 (m, 4H), 4.63 (t, J=4.8 Hz, 2H), 4.51 (t, J=4.8 Hz, 2H), 4.03 (s, 3H), 3.92 (m, 4H), 3.65 (m, 4H), 3.08 (m, 4H), 1.43 (s, 9H).

Additional compounds of the present invention (as listed in Tables 1-7 above) were similarly prepared according to the processes as described in the above schemes and examples, by selecting and substituting suitably substituted reagents, as would be readily recognized by those skilled in the art.

Biological Activity

The compounds of the present invention interrupt platelet activation induced by thrombin's proteolytic cleavage of its platelet surface receptor, and thereby inhibit platelet aggregation. Such compounds are, therefore, useful in treating platelet-mediated thrombotic disorders such as arterial and venous thrombosis, acute myocardial infarction, reocclusion following thrombolytic therapy and angioplasty, and a variety of vaso-occlusive disorders.

BIOLOGICAL EXAMPLE 1

FLIPR-based Calcium-flux Assay with Human Smooth Muscle Cells

Human aortic smooth muscle cells (HSMC) were purchased from Cascade Biologics (Portland, Oreg.) and cultured in M-231 containing smooth muscle cell growth supplement and 1× Antibiotic-Antimycotic.

To determine agonist concentration for compound testing: On the day prior to the assay, 100 µL of cells (2×105/mL) were seeded in clear, flat-bottom black-wall, tissue culture treated polystyrene 96-well plates and incubated at 37° C., 5% $CO_2$. On the day of the assay, 50 µL of complete dye loading solution (FLIPR Calcium 3 Kit, Molecular Devices) was added to each well containing 100 µL of culture media. The cells were incubated for 30-45 min at 37° C., in 5% $CO_2$ before initiating the assay on the FLIPR. The agonist effect of PAR1 peptide (S-(p-F-Phe)-Har-L-Har-KY-$NH_2$; Har=homoarginine; referred to herein as "Har" peptide) was tested and the $EC_{50}$ was determined. The $EC_{60-70}$ dose was used (30 nM) for compound testing.

Compound testing: On the day prior to the assay, 90 µL of cells (2.2×105/mL) were seeded in clear, flat-bottom blackwall, tissue culture treated polystyrene 96-well plates and incubated at 37° C., 5% $CO_2$. On the day of the assay, the test compounds were prepared at 10× in 3% DMSO Hanks buffer and 10 µL was added to each well (final DMSO concentration of 0.3%). The cells were incubated 20 min at 37° C., 5% $CO_2$. Culture medium containing testing compounds was dumped and the cells were washed four times with DPBS containing 0.1% of BSA and re-fed with 80 µL of growth medium. 70 µL of BD (fluorescent) dye was loaded to the cells and incubated 45 min at 37° C. incubator. The plates were equilibrated to room temperature for 15 min. 4× PAR1 peptide (30 nM final concentration) agonist plate and the cell plate were placed in FLIPR's assay chamber. 50 µL agonist was added to the cells and data was recorded for 5 min. Raw fluorescence data was exported for each well and tabulated versus time within an ASCII file. Data was then imported into Excel® and the peak response over basal level was determined. The percent inhibition for each test compound was calculated by the changes of fluorescent density as a % inhibition of the control Har peptide response to obtain an $IC_{50}$.

Representative compounds of the present invention were tested according to the procedure described in Biological Example 1 above, with results in Table 8 below. In Table 8 below, where multiple values are listed for a particular compound, said numbers represent individual measurements (tests) for said compound.

TABLE 8

Biological Activity

| ID No. | FLIPR-HSMC $IC_{50}$ (µM) 80-min drug incubation |
|---|---|
| 4 | 0.13, 0.068 |
| 5 | 0.032 |
| 9 | 0.16 |
| 10 | 0.109 |
| 11 | >1 |
| 12 | 0.551 |
| 13 | >3 |
| 14 | 0.78 |
| 15 | >3 |
| 16 | >1 |
| 17 | 0.90 |
| 18 | 0.19 |
| 19 | 1.0 |
| 20 | 0.44 |
| 21 | 1.1 |
| 24 | >3, >3 |
| 25 | >1, 0.44 |
| 26 | >3, >3 |
| 27 | 0.14, 0.12 |
| 32 | >3, >3 |
| 36 | 0.16, 0.14 |
| 37 | >3, >3 |
| 41 | 0.54, >1, 1.2 |
| 42 | 0.66, >1, 1.3 |
| 43 | 0.45, 0.68 |
| 44 | 0.10, 0.12 |
| 45 | 0.15, 0.18 |
| 46 | 0.094, 0.10 |
| 47 | 0.04, 0.088 |
| 48 | 0.044, 0.053 |
| 49 | 0.019, 0.059, 0.023, 0.038 |
| 51 | 0.057, 0.20, 0.22 |
| 52 | 0.025 |
| 53 | 0.189 |
| 54 | 1.1, >3, 0.75 |
| 55 | 0.006, 0.021, 0.018, 0.033, 0.035, 0.013, 0.016, 0.041, 0.068, 0.016, 0.023 |
| 58 | 0.103 |
| 59 | 0.371 |
| 60 | 0.032 |
| 61 | 0.098, 0.19 |
| 63 | 0.13, 1.3, 0.61 |
| 67 | >3, >3 |
| 68 | 0.58, 0.54 |
| 69 | 0.14, 0.11 |
| 70 | 0.052, 0.045 |
| 71 | 0.064, 0.044 |
| 72 | 0.25, 0.14 |
| 73 | 0.047, 0.057 |
| 74 | 0.15, 0.16 |
| 75 | 0.39, 0.46 |
| 76 | 0.58, 0.58 |
| 77 | 0.046, 0.074 |
| 80 | 0.073, 0.16 |
| 81 | 0.054, 0.082, 0.014 |
| 82 | 0.11, 0.17 |
| 83 | 0.24, 0.35 |
| 84 | 0.029, 0.047, 0.048, 0.011 |
| 86 | 0.20, 0.11 |
| 87 | 0.043, 0.020 |
| 88 | 0.091, 0.024 |
| 89 | 0.29, 0.13 |
| 90 | 0.68, 0.20, 0.57 |
| 91 | 0.39, 0.070, 0.19 |
| 92 | 0.53, 0.36 |
| 93 | 0.27, 0.13 |
| 94 | 0.062, 0.036 |
| 96 | 0.031, 0.015 |
| 97 | 0.050, 0.10 |

TABLE 8-continued

Biological Activity

| ID No. | FLIPR-HSMC IC$_{50}$ (μM) 80-min drug incubation |
|---|---|
| 98 | 0.27, >1 |
| 99 | 0.092, 0.22 |
| 100 | 0.022, 0.027 |
| 101 | 0.061 |
| 102 | 0.35 |
| 103 | 1.1 |
| 104 | 0.021 |

One skilled in the art will recognize that compounds which exhibit activity against Har peptide-induced smooth muscle cell intracellular calcium efflux in the above described would be indicated for the treatment of for example, thrombosis, restenosis, atherosclerosis and/or stroke.

BIOLOGICAL EXAMPLE 2

In Vitro Inhibition of Har Peptide- and Thrombin-induced Platelet Aggregation in Washed Platelets Platelet aggregation studies were performed according to the method of Bednar et al. (Bednar, B., Condra, C., Gould, R. J., and Connolly, T. M., Thromb. Res., 77:453-463 (1995)). Platelet-rich plasma (PRP) concentrates prepared from healthy volunteers who were aspirin free for at least 7 days by venipuncture using ACD-A as anticoagulant was purchased from Biological Specialties, Inc. (Colmar, Pa.). PRP was centrifuged at 730 g for 15 min. The platelet pellet was washed twice in CGS buffer (13 mM sodium citrate, 30 mM glucose, 120 mM NaCl, pH 6.5) containing 1 U/ml apyrase (grade V, Sigma-Aldrich, St. Louis, Mo.), 1 mM EGTA, and re-suspended in Tyrode's buffer (140 mM NaCl, 2.7 mM KCl, 12 mM NaHCO$_3$, 0.76 mM Na$_2$HPO$_4$, 5.5 mM dextrose, 5.0 mM HEPES, 0.2% BSA, pH 7.4). The platelets were diluted to 3×10$^8$ platelets/ml and kept >45 min at 37° C. before use. 105 μl of washed platelets, 2 mM CaCl$_2$ and 2.5 mM of fibrinogen (for PAR-1 peptide-induced platelet aggregation only) were added to a 96-well microliter plate. Platelet aggregation was initiated by the addition of serial concentrations of Har peptide or thrombin (Alpha; American Diagnostica, Cat. # 470HT, 2,500 NIH Units/mg). Buffer was added to one set of control wells. The assay plate was stirred constantly and intermittently placed in a microplate reader (Softmax, Molecular Devices, Menlo Park, Calif.) to read optical density (650 nm) at 0 and 5 minutes after the addition of the compound solutions. Aggregation was calculated as the decrease in optical density between the time 0- and 5-min measurements and expressed as % of aggregation.

For the inhibition assay, platelet aggregation measurements were conducted as described, with the additional step of test compound addition. Compounds were prepared in 100% DMSO and stored. On the day of the experiment, the compounds were diluted in the Tyrode's buffer containing 3% of DMSO as a 10× working solution. 15 μl of test compound solutions were added to 105 μl of platelets 5 min prior to CaCl$_2$ and fibrinogen additions. Platelet aggregation was initiated by the addition of agonist shown to achieve 60-70% aggregation. Antagonist potency was estimated as a % inhibition of the control Har peptide or thrombin response to obtain an IC$_{50}$.

Representative compounds of the present invention were tested according to the procedure described in Biological Example 2 above, with results in Table 9 below. In Table 9 where multiple values are listed for a particular compound, said numbers represent individual measurements (tests) for said compound.

TABLE 9

Washed platelet aggregation

| | IC$_{50}$ (μM) | |
|---|---|---|
| ID No. | Har | Thrombin |
| 49 | 0.068 | 0.107 |
| 52 | 0.172 | 0.282 |
| 58 | 0.214 | 0.304 |
| 59 | 1.250 | 2.11 |
| 73 | 0.446 | 0.813 |
| 74 | 0.779 | variable |
| 75 | 0.183 | >10 |
| 76 | 0.309 | >10 |

One skilled in the art will recognize that compounds which exhibit activity against in the above described platelet aggregation assay would be indicated for the treatment of for example, thrombosis, restenosis, atherosclerosis and/or stroke.

BIOLOGICAL EXAMPLE 3

In Vitro Inhibition of Har Peptide- and Thrombin-induced Platelet Aggregation in Platelet-rich-plasma The procedure for this assay is similar to that described in Biological Example 2, above. Briefly, platelet aggregation studies were performed according to the method of Bednar et al. (Bednar, B., Condra, C., Gould, R. J., and Connolly, T. M., Thromb. Res., 77:453-463 (1995)). Platelet-rich plasma (PRP) concentrates prepared from healthy volunteers who were aspirin free for at least 7 days by venipuncture using EDTA as anticoagulant was purchased from Biological Specialties, Inc. (Colmar, Pa.). PPP (platelet-poor-plasma) was obtained by centrifugation of PRP at Max (3,000 rpms) for 15 min at room temperature. PRP was diluted to yield platelet count of 300×10$^3$ platelets/μL with PPP. For thrombin induced platelet aggregation: 118 μL of 500 mM GPRP-NH$_2$ was added to 12 mL of 300×103 platelets before using (to clean the fibrinogen in the plasma.) GPRP was added just before the experiment. 15 μL of test compound solutions were added to 120 μL of platelets 5 min prior the agonist additions. Platelet aggregation was initiated by the addition of agonist shown to achieve 60-70% aggregation. Antagonist potency was estimated as a % inhibition of the control Har peptide or thrombin response to obtain an IC$_{50}$.

Representative compounds of the present invention were tested according to the procedure described in Biological Example 3 above, with results (IC$_{50}$) as listed in Table 10 below. Where multiple values are listed for a particular compound, said numbers represent individual measurements (tests) for said compound.

TABLE 10

Platelet Rich Plasma Aggregation

| ID No. | Har IC$_{50}$ (μM) | Thrombin IC$_{50}$ (μM) |
|---|---|---|
| 46 | 1.82, 1.04 | 4.71, 34%@10 μM |
| 47 | 2.27, 2.25 | 2.54, 2.75 |

TABLE 10-continued

Platelet Rich Plasma Aggregation

| ID No. | Har IC$_{50}$ (μM) | Thrombin IC$_{50}$ (μM) |
|---|---|---|
| 49 | 0.39 | 0.69, 2.43 |
| 55 | 2.43, >10, 11.12 | >10, >10 |
| 58 | 0.749 | 0.803 |
| 59 | 6.12 | |
| 60 | 0.709 | 0.868 |
| 61 | 0.767 | 0.79 |
| 67 | >10 | >10 |
| 68 | 33%@10 μM 38%@10 μM | 7.5 |
| 69 | 1.22, 0.98 | 0.91 |
| 70 | 0.79, 0.81 | 0.67 |
| 71 | 0.29, 0.48 | 0.38 |
| 72 | >10, >10 | >10 |
| 73 | 6.71 | 2.43, >10 |
| 74 | >10 | >10, >10 |
| 75 | 3.04 | 2.19, >10 |
| 76 | 2.06 | >10, >10 |
| 77 | 0.63, 0.49, 0.83 | 1.23, 1.92, 1.55 |
| 80 | >10, 13.14 | >10, >10 |
| 81 | >10, >10 | >10, >10 |
| 82 | 0.64, 0.93 | 2.57, 21%@10 μM |
| 83 | 0.84, 1.75 | >10, >10 |
| 84 | 2.47 | 2.51 |
| 86 | 3.68 | 2.2 |
| 87 | 7.38, >10 | >10, >10 |
| 88 | 1.63, 1.21 | 3.55, 2.66 |
| 89 | 1.28, 2.31 | 4.88, 4.61, 6.02 |
| 90 | 2.56, 4.45 | 30%@10 μM, >10 |
| 91 | 12.9, 26%@10 μM | >10, >10 |
| 92 | 24%@10 μM | >10, >10 |
| 93 | 2.08, 3.8 | >10, >10 |
| 94 | 2.21, 2.32 | 2.49, 3.34 |
| 96 | 1.57, 2.3 | 3.23, 3.25 |
| 97 | 1.3 | 2.19 |
| 98 | >10 | >10 |
| 99 | >10 | 23%@10 μM |
| 100 | 1.61 | 1.92 |

One skilled in the art will recognize that compounds which exhibit activity against in the above described platelet aggregation assay would be indicated for the treatment of for example, thrombosis, restenosis, atherosclerosis and/or stroke.

Solid Dosage, Oral Formulation

Prophetic Example

As a specific embodiment of an oral composition, 100 mg of the Compound #55, prepared as in Example 2, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

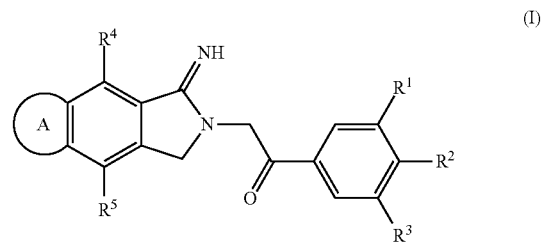

wherein $R^1$ is $C_{3-6}$alkyl;

$R^2$ is selected from the group consisting of hydroxy and $C_{1-4}$alkoxy;

$R^3$ is selected from the group consisting of hydrogen, halogen, $C_{3-6}$alkyl, 1-pyrrolidinyl, 1-piperidinyl, 1-piperazinyl, 4-morpholinyl and 4-thiomorpholinyl; wherein the 1-pyrrolidinyl, 1-piperidinyl, 1-piperazinyl, 4-morpholinyl or 4-thiomorpholinyl is optionally substituted with a substituent selected from the group consisting of $C_{1-4}$alkyl;

alternatively, $R^2$ and $R^3$ are taken together with the carbon atoms to which they are bound to form 2,3-morpholinyl or 2,3-(4-methyl-morpholinyl);

$R^4$ is selected from the group consisting of hydrogen and halogen;

$R^5$ is selected from the group consisting of hydrogen and halogen; provided that $R^4$ and $R^5$ are not each halogen;

is selected from the group consisting of formulas (a) through (e);

(a)

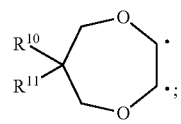

wherein $R^{10}$ is selected from the group consisting of hydrogen, halogen and $C_{1-4}$alkyl;

$R^{11}$ is selected from the group consisting of hydrogen, fluoro, $C_{1-2}$alkyl, —$CH_2$—C(O)H —($C_{1-4}$alkyl)-OH, —$CH_2CH(OC_{1-2}$alkyl$)_2$ and —($C_{1-4}$alkyl)-$NR^AR^B$;

wherein $R^A$ and $R^B$ are each independently selected from the group consisting of hydrogen and $C_{1-4}$alkyl;

alternatively, $R^A$ and $R^B$ are taken together with the nitrogen atom to which they are bound to form a monocyclic nitrogen-containing heterocyclyl group; and wherein the monocyclic nitrogen-containing heterocyclyl group is optionally substituted with $C_{1-4}$alkyl;

(b)

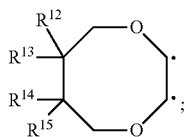

wherein $R^{12}$, $R^{13}$, $R^{14}$ and $R^{15}$ are each hydrogen or are each fluoro;

alternatively, $R^{12}$ and $R^{14}$ are taken together as an electron pair to form a bond between the carbon atoms to which they are bound; and $R^{13}$ and $R^{15}$ are each hydrogen;

alternatively, $R^{12}$ and $R^{14}$ are taken together as an electron pair to form a bond between the carbon atoms to which they are bound; and $R^{13}$ and $R^{15}$ are taken together with the carbon atoms to which they are bound to form a bridging group selected from the group consisting of

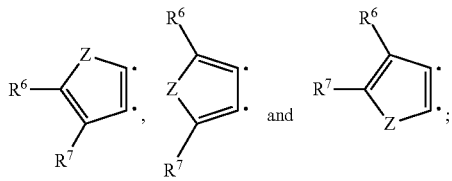

wherein Z is selected from the group consisting of O and S; and wherein $R^6$ and $R^7$ are each independently selected from the group consisting of $C_{1-4}$alkyl and —C(O)O—($C_{1-4}$alkyl);

(c)

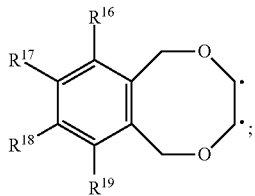

wherein $R^{16}$, $R^{17}$, $R^{18}$ and $R^{19}$ are each independently selected from the group consisting of hydrogen, halogen, nitro, $C_{1-4}$alkyl, —C(O)OH and —C(O)O—($C_{1-4}$alkyl); provided that at least two of $R^{16}$, $R^{17}$, $R^{18}$ and $R^{19}$ are hydrogen;

alternatively, $R^{16}$ and $R^{19}$ are each hydrogen; and $R^{17}$ and $R^{18}$ are taken together with the carbon atoms to which they are bound to form 4,5-([1,3]-dioxolanyl);

(d)

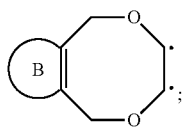

wherein

is selected from the group consisting of

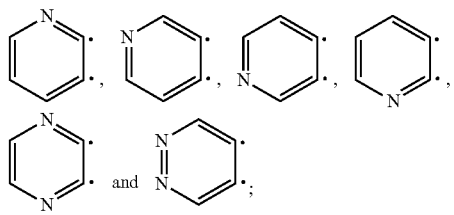

and (e)

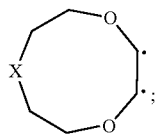

wherein X is N—$R^{20}$; and wherein $R^{20}$ is selected from the group consisting of hydrogen, phenyl, —C(O)—$C_{1-4}$alkyl, —C(O)O-t-butyl and —$SO_2$-(4-tolyl);

or a pharmaceutically acceptable salt thereof.

2. A compound as in claim 1, wherein
$R^1$ is $C_{3-5}$alkyl;
$R^2$ is selected from the group consisting of hydroxy and $C_{1-2}$alkoxy;
$R^3$ is selected from the group consisting of hydrogen, halogen, $C_{3-6}$alkyl, 1-piperidinyl, 1-piperazinyl and 4-morpholinyl; wherein the 1-piperidinyl, 1-piperazinyl or 4-morpholinyl is optionally substituted with $C_{1-4}$alkyl;
alternatively, $R^2$ and $R^3$ are taken together with the carbon atoms to which they are bound to form 2,3-morpholinyl or 2,3-(4-methyl-morpholinyl);
$R^4$ is selected from the group consisting of hydrogen and fluoro; and $R^5$ is selected from the group consisting of hydrogen and fluoro; provided that $R^4$ and $R^5$ are not each fluoro;
$R^A$ and $R^B$ are each independently selected from the group consisting of hydrogen and $C_{1-2}$alkyl;
alternatively, $R^A$ and $R^B$ are taken together with the nitrogen atom to which they are bound to form a monocyclic nitrogen-containing heterocyclyl group; and wherein the monocyclic nitrogen-containing heterocyclyl group is optionally substituted with $C_{1-2}$alkyl;
Z is selected from the group consisting of S and O;
$R^6$ and $R^7$ are each independently selected from the group consisting of $C_{1-2}$alkyl and —C(O)O—($C_{1-2}$alkyl);
$R^{16}$, $R^{17}$, $R^{18}$ and $R^{19}$ are each independently selected from the group consisting of hydrogen, halogen, nitro, $C_{1-2}$alkyl, —C(O)O—($C_{1-2}$alkyl) and —$CO_2$H; provided that at least two of $R^{16}$, $R^{17}$, $R^{18}$ and $R^{19}$ are hydrogen;
alternatively, $R^{16}$ and $R^{19}$ are each hydrogen; and $R^{17}$ and $R^{18}$ are taken together with the carbon atoms to which they are bound to form 4,5-([1,3]-dioxolanyl); and

is selected from the group consisting of

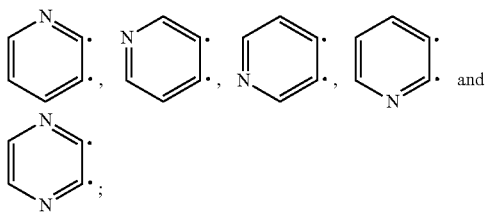

or a pharmaceutically acceptable salt thereof.

3. A compound as in claim 2, wherein $R^1$ is $C_4$alkyl;

$R^3$ is selected from the group consisting of hydrogen, halogen, $C_{3-6}$alkyl, 1-piperazinyl and 4-morpholinyl; wherein the 1-piperazinyl is optionally substituted with a substituent selected from the group consisting of $C_{1-4}$alkyl;

alternatively, $R^2$ and $R^3$ are taken together with the carbon atoms to which they are bound to form 2,3-morpholinyl or 2,3-(4-methyl-morpholinyl);

$R^{10}$ is selected from the group consisting of hydrogen, halogen and $C_{1-2}$alkyl;

$R^{11}$ is selected from the group consisting of hydrogen, fluoro, $C_{1-2}$alkyl, —$CH_2$—C(O)H, —($C_{1-2}$alkyl)-OH, —$CH_2$—$CH(OC_{1-2}alkyl)_2$ and —($C_{1-2}$alkyl)-$NR^AR^B$;

Z is S; and $R^6$ and $R^7$ are each independently selected from the group consisting of methyl and methoxy-carbonyl-;

or a pharmaceutically acceptable salt thereof.

4. A compound as in claim 3, wherein $R^2$ is selected from the group consisting of hydroxy and methoxy;

$R^3$ is selected from the group consisting of hydrogen, bromo, t-butyl, 4-morpholinyl and 1-(4-methyl-piperazinyl);

alternatively, $R^2$ and $R^3$ are taken together with the carbon atoms to which they are bound to form 2,3-morpholinyl or 2,3-(4-methyl-morpholinyl);

$R^{10}$ is selected from the group consisting of hydrogen, fluoro and methyl;

$R^{11}$ is selected from the group consisting of hydrogen, fluoro, methyl, —$CH_2$—C(O)H, —$CH_2CH_2$—OH, —$CH_2$—$CH(OCH_2CH_3)_2$, methylamino-ethyl-, dimethylamino-ethyl-, 4-morpholinyl-ethyl-, 1-(4-methyl-piperazinyl), 2-thiazolidinyl-methyl-, 3-thiazolidinyl-ethyl- and 1-pyrrolidinyl-ethyl-;

$R^{13}$ and $R^{15}$ are taken together with the carbon atoms to which they are bound to form a bridging group selected from the group consisting of

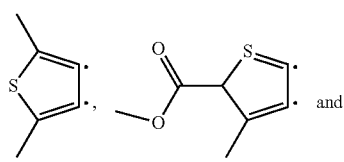

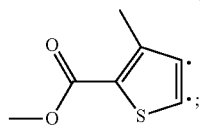

$R^{16}$, $R^{17}$, $R^{18}$ and $R^{19}$ are each independently selected from the group consisting of hydrogen, fluoro, nitro, methyl, methoxy-carbonyl- and carboxy; provided that at least $R^{16}$ and $R^{19}$ or $R^{17}$ and $R^{18}$ are each hydrogen;

alternatively, $R^{16}$ and $R^{19}$ are each hydrogen; and $R^{17}$ and $R^{18}$ are taken together with the carbon atoms to which they are bound to form 4,5-([1,3]-dioxolanyl); and $R^{20}$ is selected from the group consisting of hydrogen, phenyl, —C(O)-methyl, —C(O)O-t-butyl and —$SO_2$-(4-tolyl);

or a pharmaceutically acceptable salt thereof.

5. A compound as in claim 4, wherein $R^{11}$ is selected from the group consisting of hydrogen, fluoro, methyl, —$CH_2$—$CH(OCH_2CH_3)_2$, 2-thiazolidinyl-methyl- and 3-thiazolidinyl-ethyl-; and $R^{20}$ is selected from the group consisting of —C(O)O-t-butyl and —$SO_2$-(4-tolyl);

or a pharmaceutically acceptable salt thereof.

6. A compound as in claim 5, wherein $R^3$ is selected from the group consisting of hydrogen, t-butyl, 4-morpholinyl and 1-(4-methyl-piperazinyl);

alternatively, $R^2$ and $R^3$ are taken together with the carbon atoms to which they are bound to form 2,3-morpholinyl or 2,3-(4-methyl-morpholinyl);

$R^{10}$ is selected from the group consisting of hydrogen and methyl;

$R^{11}$ is selected from the group consisting of hydrogen, methyl, 2-thiazolidinyl-methyl- and 3-thiazolidinyl-ethyl-;

$R^{13}$ and $R^{15}$ are taken together with the carbon atoms to which they are bound to form a bridging group selected from the group consisting of

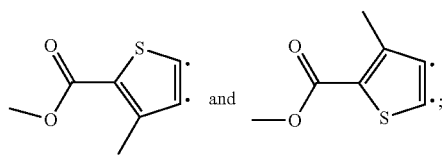

or a pharmaceutically acceptable salt thereof.

7. A compound as in claim 6, wherein $R^3$ is selected from the group consisting of t-butyl, 4-morpholinyl and 1-(4-methyl-piperazinyl);

alternatively, $R^2$ and $R^3$ are taken together with the carbon atoms to which they are bound to form 2,3-(4-methyl-morpholinyl);

is selected from the group consisting of formulas (b), (c) and (d);

$R^{12}$, $R^{13}$, $R^{14}$ and $R^{15}$ are each hydrogen;

alternatively, $R^{12}$ and $R^{14}$ are taken together as an electron pair to form a bond between the carbon atoms to which they are bound; and $R^{13}$ and $R^{15}$ are each hydrogen; and

is selected from the group consisting of

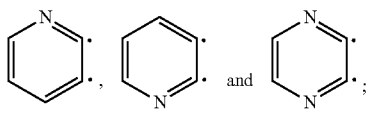

or a pharmaceutically acceptable salt thereof.

8. A compound as in claim 7, wherein
$R^3$ is selected from the group consisting of t-butyl and 4-morpholinyl;
alternatively, $R^2$ and $R^3$ are taken together with the carbon atoms to which they are bound to form 2,3-(4-methyl-morpholinyl);
$R^4$ is hydrogen;
$R^5$ is hydrogen;
$R^{16}$ is hydrogen;
$R^{17}$ is selected from the group consisting of hydrogen, nitro and methoxy-carbonyl-;
$R^{18}$ is selected from the group consisting of hydrogen and nitro;
$R^{19}$ is hydrogen;
provided that one of $R^{17}$ or $R^{18}$ is hydrogen; and

is selected from the group consisting of

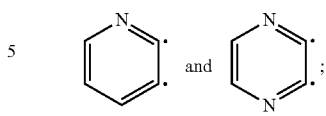

or a pharmaceutically acceptable salt thereof.

9. A pharmaceutical composition comprising a pharmaceutically acceptable carrier and a compound of claim 1.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

12. A method of treating a disorder mediated by the PAR-1 thrombin receptor, wherein the disorder mediated by the PAR-1 thrombin receptor is selected from the group consisting of thrombosis and restenosis, comprising administering to a subject in need thereof a therapeutically effective amount of the compound of claim 1.

13. A method of treating a disorder mediated by the PAR-1 thrombin receptor wherein the disorder is selected from the group consisting of thrombosis and restenosis, comprising administering to a subject in need thereof a therapeutically effective amount of the composition of claim 9.

14. A method of treating a condition selected from the group consisting of thrombosis and restenosis, comprising administering to a subject in need thereof a therapeuticallym effective amount of the compound of claim 1.

15. A compound of formula (I) selected from the group consisting of:

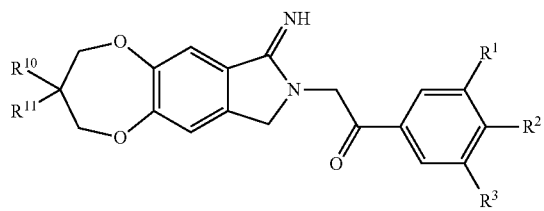

| ID No. | $R^{10}$ | $R^{11}$ | $R^1$ | $R^2$ | $R^3$ |
|---|---|---|---|---|---|
| 4 | H | H | t-butyl | hydroxy | t-butyl; |
| 9 | methyl | methyl | t-butyl | hydroxy | t-butyl; |
| 12 | H | 4-morpholinyl-ethyl- | t-butyl | hydroxy | t-butyl; |
| 13 | H | 1-pyrrolidinyl-ethyl- | t-butyl | hydroxy | t-butyl; |
| 14 | H | —CH2—C(O)H | t-butyl | hydroxy | t-butyl; |
| 15 | H | 1-(4-methyl-piperazinyl)-ethyl | t-butyl | hydroxy | t-butyl; |
| 16 | H | dimethyl-amino-ethyl- | t-butyl | hydroxy | t-butyl; |
| 17 | H | 1-(2-hydroxy-ethyl) | t-butyl | hydroxy | t-butyl; |
| 37 | H | methyl-amino-ethyl- | t-butyl | hydroxy | t-butyl; |
| 43 | H | 4-morpholinyl-ethyl- | t-butyl | methoxy | 4-morpholinyl; |
| 44 | H | 2-thiazolidinyl-methyl | t-butyl | methoxy | 4-morpholinyl; |
| 45 | H | 3-thiazolidinyl-ethyl | t-butyl | methoxy | 4-morpholinyl; |
| 92 | fluoro | fluoro | t-butyl | methoxy | 4-morpholinyl; |
| 93 | fluoro | fluoro | t-butyl | hydroxy | t-butyl; |

-continued

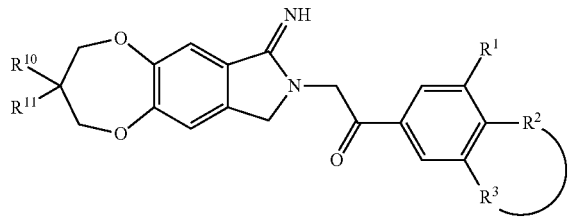

| ID No. | R¹⁰ | R¹¹ | R¹ | R² + R³ taken together with C atoms |
|---|---|---|---|---|
| 19 | H | H | t-butyl | 2,3-(4-methyl-morpholinyl); |
| 20 | H | 1-(2,2-diethoxy)-ethyl- | t-butyl | 2,3-(4-methyl-morpholinyl); |
| 21 | H | 4-morpholinyl-ethyl- | t-butyl | 2,3-(4-methyl-morpholinyl); |
| 24 | H | 1-pyrrolidinyl-ethyl- | t-butyl | 2,3-(4-methyl-morpholinyl); |
| 25 | H | 1-(2-hydroxy-ethyl) | t-butyl | 2,3-(4-methyl-morpholinyl); |
| 26 | H | 4-methyl-piperazinyl-ethyl- | t-butyl | 2,3-(4-methyl-morpholinyl); |
| 27 | H | 3-thiazolidinyl-ethyl | t-butyl | 2,3-(4-methyl-morpholinyl); |
| 32 | H | dimethyl-amino-ethyl- | t-butyl | 2,3-(4-methyl-morpholinyl); |
| 36 | H | H | t-butyl | 2,3-morpholinyl; |

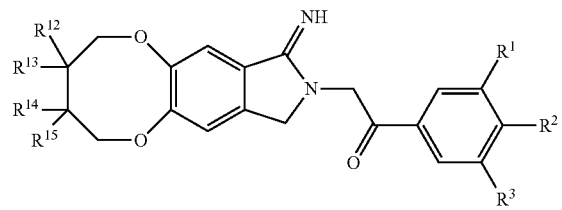

| ID No. | R¹², R¹³, R¹⁴, R¹⁵ | R¹ | R² | R³ |
|---|---|---|---|---|
| 5 | H, H, H, H | t-butyl | hydroxy | t-butyl; |
| 90 | F, F, F, F | t-butyl | methoxy | 4-morpholinyl; |
| 91 | F, F, F, F | t-butyl | hydroxy | t-butyl; |

| ID | R¹², R¹³, R¹⁴, R¹⁵ | R¹ | R² + R³ taken together with C atoms |
|---|---|---|---|
| 18 | H, H, H, H | t-butyl | 2,3-(4-methyl-morpholinyl); |

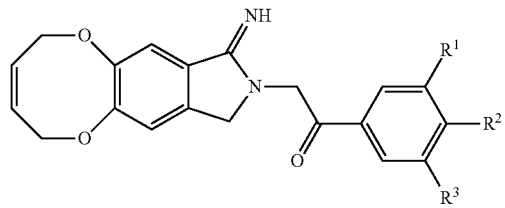

| ID No. | R¹ | R² | R³ |
|---|---|---|---|
| 97 | t-butyl | methoxy | 4-morpholinyl; |
| 100 | t-butyl | hydroxy | t-butyl; |

-continued

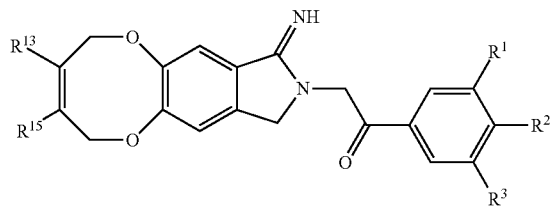

| ID No. | R¹³ + R¹⁵ taken together with C atoms | R¹ | R² | R³ |
|---|---|---|---|---|
| 74 | (2,5-dimethylthiophene) | t-butyl | hydroxy | t-butyl; |
| 101 | (methyl 3-methylthiophene-2-carboxylate) or (methyl 3-methylthiophene-2-carboxylate isomer) | t-butyl | hydroxy | t-butyl; |

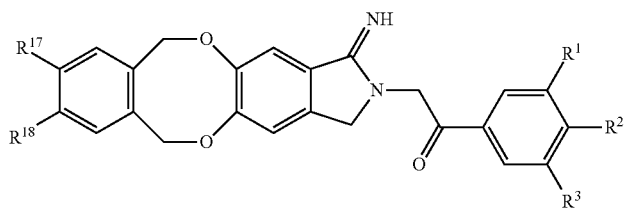

| ID No. | R¹⁷ | R¹⁸ | R¹ | R² | R³ |
|---|---|---|---|---|---|
| 46 | H | H | t-butyl | methoxy | 4-morpholinyl; |
| 47 | H | H | t-butyl | hydroxy | t-butyl; |
| 53 | methoxy-carbonyl- | H | t-butyl | methoxy | bromo; |
| 55 | methoxy-carbonyl- | H | t-butyl | hydroxy | t-butyl; |
| 72 | carboxy | H | t-butyl | hydroxy | t-butyl; |
| 73 | methoxy-carbonyl- | H | t-butyl | methoxy | 4-morpholinyl; |
| 80 | H | methoxy-carbonyl- | t-butyl | hydroxy | t-butyl; |
| 81 | H | carboxy- | t-butyl | hydroxy | t-butyl; |
| 84 | nitro | H | t-butyl | hydroxy | t-butyl; |
| mixture of 85 | H | nitro | t-butyl | hydroxy | t-butyl; |
| 85 | fluoro | fluoro | t-butyl | hydroxy | t-butyl; |
| 89 | fluoro | fluoro | t-butyl | methoxy | 4-morpholinyl; |
| 98 | methyl | methyl | t-butyl | methoxy | 4-morpholinyl; |
| 99 | methyl | methyl | t-butyl | hydroxy | t-butyl; |
| 102 | methoxy-carbonyl- | methoxy-carbonyl- | t-butyl | hydroxy | t-butyl; |
| 103 | methoxy-carbonyl- | methoxy-carbonyl- | t-butyl | methoxy | 4-morpholinyl; |
| 104 | nitro | H | t-butyl | methoxy | 4-morpholinyl; |
|  | H | nitro | t-butyl | methoxy | 4-morpholinyl; |

-continued

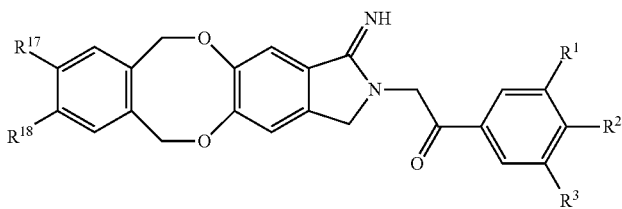

| ID No. | R¹⁷ + R¹⁸ taken together with C atoms | R¹ | R² | R³ |
|---|---|---|---|---|
| 59 | (4,5-([1,3]-dioxolanyl) | t-butyl | methoxy | 4-morpholinyl; |

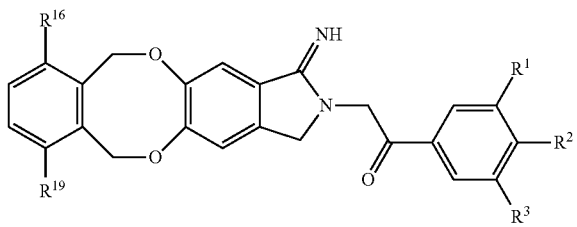

| ID No. | R¹⁶ | R¹⁹ | R¹ | R² | R³ |
|---|---|---|---|---|---|
| 87 | fluoro | fluoro | t-butyl | hydroxy | t-butyl; |
| 88 | fluoro | fluoro | t-butyl | methoxy | 4-morpholinyl; |

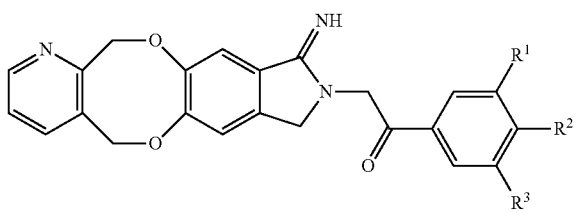

| ID No. | R¹ | R² | R³ |
|---|---|---|---|
| 49 | t-butyl | hydroxy | t-butyl; |
| 52 | t-butyl | methoxy | 4-morpholinyl; |
| 54 | t-butyl | methoxy | Bromo; |
| 75 | t-butyl | methoxy | t-butyl; |
| 82 | t-butyl | hydroxy | H; |

| ID No. | R¹ | R² + R³ taken together with C atoms |
|---|---|---|
| 70 | t-butyl | 2,3-(4-methyl-morpholiny); |

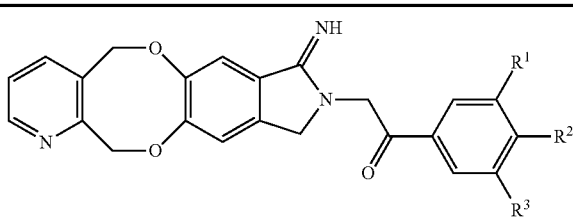

| ID No. | R¹ | R² | R³ |
|---|---|---|---|
| 48 | t-butyl | hydroxy | t-butyl; |
| 51 | t-butyl | methoxy | 4-morpholinyl; |
| 71 | t-butyl | methoxy | 1-(4-methyl-piperazinyl); |
| 76 | t-butyl | methoxy | t-butyl; |
| 83 | t-butyl | hydroxy | H; |

-continued

| ID | R¹ | R² + R³ taken together with C atoms |
|---|---|---|
| 69 | t-butyl | 2,3-(4-methyl-morpholinyl); |

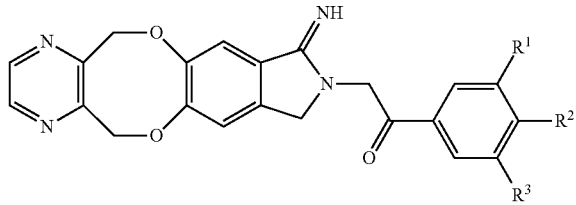

| ID No. | R¹ | R² | R³ |
|---|---|---|---|
| 58 | t-butyl | methoxy | 4-morpholinyl; |
| 77 | t-butyl | hydroxy | t-butyl; |

| ID No. | R¹ | R² + R³ taken together with C atoms |
|---|---|---|
| 60 | t-butyl | 2,3-(4-methyl-morpholinyl); |

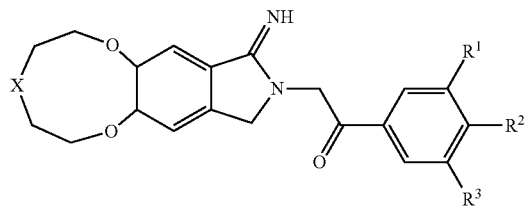

| ID No. | X | R¹ | R² | R³ |
|---|---|---|---|---|
| 10 | N—C(O)O-4-butyl | t-butyl | hydroxy | t-butyl; |
| 11 | NH | t-butyl | hydroxy | t-butyl; |
| 41 | N—C(O)O-t-butyl | t-butyl | methoxy | 4-morpholinyl; |
| 42 | NH | t-butyl | methoxy | 4-morpholinyl; |
| 63 | N—SO₂-(4-tolyl) | t-butyl | methoxy | 4-morpholinyl; |
| 67 | N—C(O)—CH₃ | t-butyl | methoxy | 4-morpholinyl; |
| 68 | N-phenyl | t-butyl | methoxy | 4-morpholinyl; |

| ID No. | Structure |
|---|---|
| 61 | 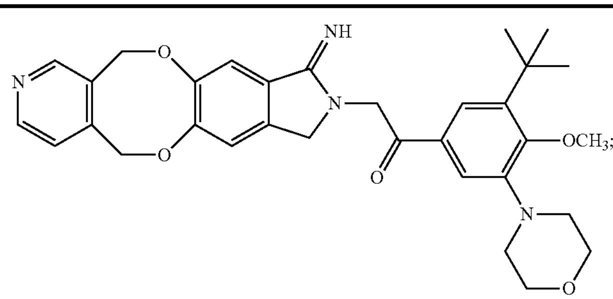 |

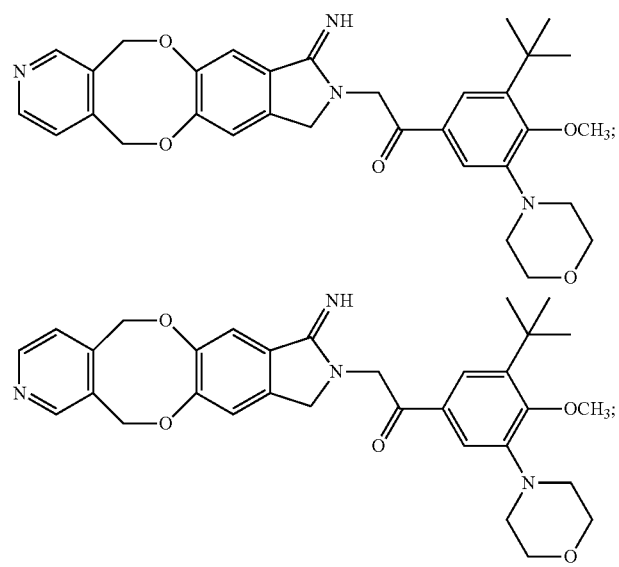

94 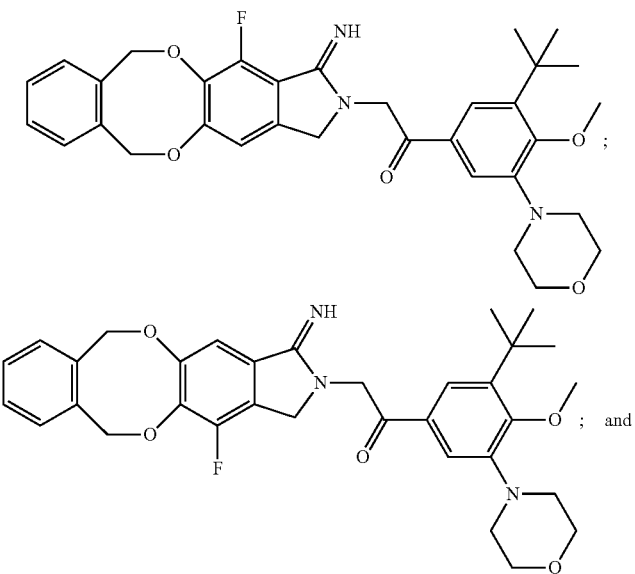
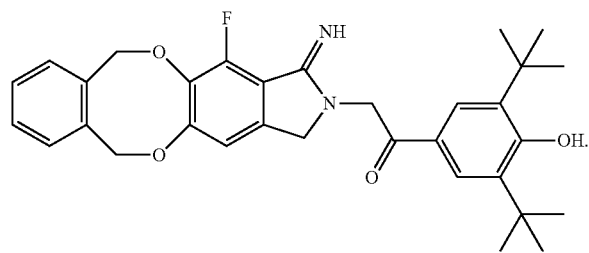 [SMILES: CC(C)(C)c1cc(C(=O)CN2Cc3cc4c(c(F)c3C2=N)OCc2ccccc2CO4)cc(C(C)(C)C)c1O]
96